(12) United States Patent
Watanabe

(10) Patent No.: US 7,446,197 B2
(45) Date of Patent: Nov. 4, 2008

(54) METAL-COMPLEX COMPOUND AND ORGANIC ELECTROLUMINESCENCE DEVICE USING THE COMPOUND

(75) Inventor: Masami Watanabe, Chiba (JP)

(73) Assignee: Idemitsu Kosan Co., Ltd., Tokyo (JP)

( * ) Notice: Subject to any disclaimer, the term of this patent is extended or adjusted under 35 U.S.C. 154(b) by 0 days.

(21) Appl. No.: 11/558,725

(22) Filed: Nov. 10, 2006

(65) Prior Publication Data

US 2007/0108891 A1    May 17, 2007

Related U.S. Application Data

(60) Provisional application No. 60/735,816, filed on Nov. 14, 2005.

(51) Int. Cl.
*C07F 15/00* (2006.01)
*H01J 1/62* (2006.01)

(52) U.S. Cl. .............................. 546/2; 548/101; 313/504

(58) Field of Classification Search ..................... 546/2; 548/101; 313/504
See application file for complete search history.

(56) References Cited

FOREIGN PATENT DOCUMENTS

WO    WO 2006/008976 A1    1/2006

OTHER PUBLICATIONS

Robert Frånkel, et al., Homoleptic carbene complexes Part IX. Bis(imidazolin-2ylidene-1-yl)borate complexes of palladium(II), platinum(III) and gold(I), Inorganica Chimica Acta, vol. 312, No. 1-2, 2001, p. 23-39.
U.S. Appl. No. 11/559,644, filed Nov. 14, 2006, Watanabe.
U.S. Appl. No. 11/558,725, filed Nov. 10, 2006, Watanabe.
U.S. Appl. No. 11/557,576, filed Nov. 8, 2006, Watanabe.

*Primary Examiner*—P. Nazario Gonzalez
(74) *Attorney, Agent, or Firm*—Oblon, Spivak, McClelland, Maier & Neustadt, P.C.

(57) ABSTRACT

A metal complex compound having a specific structure having a metal such as iridium, and an organic electroluminescence device which has an organic thin film layer having one layer or a plurality of layers including at least a light emitting layer and disposed between a pair of electrodes and contains the metal complex in at least one layer in the organic thin film layer. The organic electroluminescence device exhibits a great efficiency of light emission and has a long life due to the metal complex compound.

8 Claims, No Drawings

METAL-COMPLEX COMPOUND AND ORGANIC ELECTROLUMINESCENCE DEVICE USING THE COMPOUND

TECHNICAL FIELD

The present invention relates to a metal complex compound and an organic electroluminescence device using the compound, and more particularly to an organic electroluminescence device exhibiting a great efficiency of light emission and having a long life and a novel metal complex compound for realizing the device.

Background Art

An organic electroluminescence ("electroluminescence" will be referred to as "EL", hereinafter) device is a spontaneous light emitting device which utilizes the principle that a fluorescent substance emits light by energy of recombination of holes injected from an anode and electrons injected from a cathode when an electric field is applied. Since an organic EL device of the laminate type driven under a low electric voltage was reported by C. W. Tang of Eastman Kodak Company (C. W. Tang and S. A. Vanslyke, Applied Physics Letters, Volume 51, Pages 913, 1987), many studies have been conducted on organic EL devices using organic materials as the constituting materials. Tang et al. used a laminate structure using tris(8-hydroxyquinolinolato)aluminum for the light emitting layer and a triphenyldiamine derivative for the hole transporting layer. Advantages of the laminate structure are that the efficiency of hole injection into the light emitting layer can be increased, that the efficiency of forming excited particles which are formed by blocking and recombining electrons injected from the cathode can be increased, and that excited particles formed within the light emitting layer can be enclosed. As the structure of the organic EL device, a two-layered structure having a hole transporting (injecting) layer and an electron transporting light emitting layer and a three-layered structure having a hole transporting (injecting) layer, a light emitting layer and an electron transporting (injecting) layer are well known. To increase the efficiency of recombination of injected holes and electrons in the devices of the laminate type, the structure of the device and the process for forming the device have been studied.

As the light emitting material of the organic EL device, chelate complexes such as tris(8-quinolinolato)aluminum, coumarine derivatives, tetraphenylbutadiene derivatives, distyrylarylene derivatives and oxadiazole derivatives are known. It is reported that light in the visible region ranging from blue light to red light can be obtained by using these light emitting materials, and development of a device exhibiting color images is expected (For example, Patent Reference 1, Patent Reference 2 and Patent Reference 3).

It is recently proposed that an organic phosphorescent material other than a fluorescent material is used in the light emitting layer of an organic EL device (for example, Non-Patent Reference 1 and Non-Patent Reference 2). As described above, a great efficiency of light emission is achieved by utilizing a phosphorescent material excited to the singlet state and the triplet state in the light emitting layer of an organic EL device. It is considered that singlet excimers and triplet excimers are formed in relative amounts of 1:3 due to the difference in the multiplicity of spin when electrons and holes are recombined in an organic EL device. Therefore, it is expected that an efficiency of light emission 3 to 4 times as great as that of a device utilizing fluorescence alone can be achieved by utilizing a material emitting phosphorescent light.

In the organic EL devices described above, a construction formed by successively laminating layers such as an anode, a hole transporting layer, an organic light emitting layer, an electron transporting layer (a hole barrier layer), an electron transporting layer and a cathode is used so that the excited state of the triplet or excimers of the triplet do not disappear, and a host compound and a phosphorescent compound are used for the organic light emitting layer (for example, Patent Reference 4 and Patent Reference 5). In these patent references, technology on phosphorescent materials emitting red to green light is disclosed. Technology on light emitting materials emitting bluish light is also disclosed (for example, Patent Reference 6, Patent Reference 7 and Patent Reference 8). However, devices in accordance with the above technology have very short lives. In particular, in Patent Reference 7 and Patent Reference 8, skeleton structures of ligands in which Ir metal and phosphorus atom are bonded is described. The bonding in these structures is weak, and heat resistance is markedly poor although the emitted light is bluish. In Patent Reference 9, a complex in which oxygen atom and nitrogen atom are bonded to a central metal atom is described. However, specific effects of the group bonded to oxygen atom are obscure since no descriptions can be found. In Patent Reference 10, a complex in which nitrogen atoms contained in different cyclic structures are each bonded to a central metal atom is disclosed. A device prepared by using the complex exhibits an outer quantum efficiency as small as 5% although bluish light is emitted.

In Non-Patent Reference 3, synthesis of a bis[N,C$^{2'}$-(2-phenylpyridino)]iridium complex having an auxiliary ligand having pyrazolyl group crosslinked with a borate (for example, tetrakispyrazolyl borate anion) and spectra of absorption and emission of ultraviolet and visible light by the complex are described. It is shown that the electron density of iridium atom is decreased due to the effect of an electron-attracting auxiliary ligand such as tetrakispyrazolyl borate anion, and the HOMO orbital at the center of the metal is stabilized, and that the wavelength of the light emission decreases due to this effect. However, no descriptions are found on the preparation of an organic EL device, and no results on the heat stability, the possibility of vacuum deposition or the life of light emission are disclosed.

In addition to the above Non-Patent Reference 3, in Non-Patent Reference 4, it is shown that the wavelength of the light emission is further decreased by providing an ionic property to the auxiliary ligand (for example, [(tpy)$_2$Ir(dppe)] (CF$_3$SO$_3$)). However, similarly to the above Non-Patent Reference, no descriptions are found on the preparation of an organic EL device, and no results on the heat stability, the possibility of vacuum deposition or the life of light emission are disclosed.

[Patent Reference 1] Japanese Patent Application Laid-Open No. Heisei 8(1996)-239655

[Patent Reference 2] Japanese Patent Application Laid-Open No. Heisei 7(1995)-183561

[Patent Reference 3] Japanese Patent Application Laid-Open No. Heisei 3(1991)-200289

[Patent Reference 4] U.S. Pat. No. 6,097,147

[Patent Reference 5] International Patent Publication No. WO 01/41512

[Patent Reference 6] United States Patent Application Laid-Open No. 2001/0025108

[Patent Reference 7] United States Patent Application Laid-Open No. 2002/0182441

[Patent Reference 8] Japanese Patent Application Laid-Open No. 2002-170684

[Patent Reference 9] Japanese Patent Application Laid-Open No. 2003-123982

[Patent Reference 9] Japanese Patent Application Laid-Open No. 2003-133074

[Non-Patent Reference 1] D. F. O'Brien, M. A. Baldo et al., "Improved energy transfer in electrophosphorescent devices", Applied Physics letters, Vol. 74, No. 3, pp 442 to 444, Jan. 18, 1999

[Non-Patent Reference 2] M. A. Baldo et al., "Very high-efficiency green organic light-emitting devices based on electrophosphorescence", Applied Physics letters, Vol. 75, No. 1, pp 4-6, Jul. 5, 1999

[Non-Patent Reference 3] Polyhedron 23, 2004, 419

[Non-Patent Reference 4] Inorganic Chemistry, 44, No. 6, 2005, 1713

DISCLOSURE OF THE INVENTION

Problems to be Overcome by the Invention

The present invention has been made to overcome the above problems and has an object of providing an organic EL device exhibiting a great efficiency of light emission and has a long life and a novel metal complex compound for realizing the device and providing technology for facilitating the molecular design of the light emitting material for adjusting the color of the emitted light.

Means for Overcoming the Problems

As the result of intensive studies by the present inventors to achieve the above object, it was found that an organic EL device exhibiting a great efficiency of light emission and having a long life could be obtained by using a transition metal complex compound having a metal-carbene bond represented by general formula (1) shown in the following. The present invention has been completed based on the knowledge.

The present invention provides:

(a) A metal complex compound having a metal-carbene bond represented by following general formula (1):

[In general formula (1), M represents iridium atom or platinum atom, $L^1$ and $L^2$ represent bidentate ligands different from each other, a partial structure represented by $(L^1)_m M$ is represented by following general formula (2), a partial structure represented by $M(L^2)_n$ is represented by following general formula (3), m represents an integer of 0 to 2, n represents an integer of 1 to 3, and m+n represents a valence of the metal represented by M.

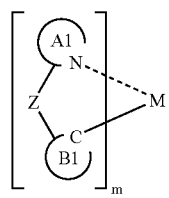

{In general formula (2), N and C represent nitrogen atom and carbon atom, respectively, ring A1 represents an aromatic heterocyclic group having 3 to 50 nuclear atoms including nitrogen atom which may have substituents, ring B1 represents an aryl group having 6 to 50 nuclear carbon atoms which may have substituents, and ring A1 and ring B1 are bonded with covalent bonds via Z, wherein Z represents a single bond, —O—, —S—, —CO—, —(CR'R")$_a$—, —(SiR'R")$_a$— or —NR'—, (R' and R" each independently represent hydrogen atom, an aryl group having 6 to 50 nuclear carbon atoms which may have substituents, an aromatic heterocyclic group having 3 to 50 nuclear atoms which may have substituents or an alkyl group having 1 to 50 carbon atoms which may have substituents, a represents an integer of 1 to 10, and the atoms and the groups represented by R' and R" may be a same with or different from each other.)}

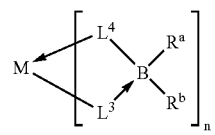

{In general formula (3), B represents boron atom, $L^3$ and $L^4$ each represent a crosslinking group having a covalent bond (shown by a solid line) and a coordinate bond (shown by an arrow), at least one of $L^3$ and $L^4$ represents an aromatic heterocyclic group having 3 to 50 nuclear atoms including nitrogen atom which has a coordinate bond with carbene carbon atom and may have substituents, $R^a$ and $R^b$ each independently represent hydrogen atom, an alkyl group having 1 to 50 carbon atoms which may have substituents, an alkenyl group having 2 to 50 carbon atoms which may have substituents, an aryl group having 6 to 50 nuclear carbon atoms which may have substituents or an aromatic heterocyclic group having 3 to 50 nuclear atoms which may have substituents, and groups represented by $L^3, L^4, R^a$ and $R^b$ may be bonded to each other to form a cyclic structure.}];

(b) A metal complex compound having a metal-carbene bond described in (a), wherein the partial structure represented by $(L^1)_m M$ which is represented by general formula (2) is a partial structure represented by following general formula (4):

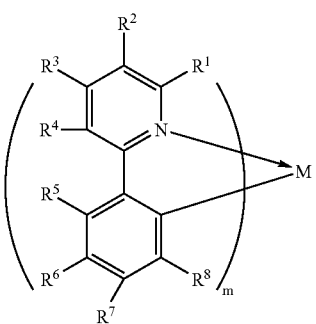

(In the above formula, $R^1$ to $R^8$ each independently represent hydrogen atom, an alkyl group having 1 to 30 carbon atoms which may have substituents, a halogenated alkyl group having 1 to 30 carbon atoms which may have substituents, an alkoxyl group having 1 to 30 carbon atoms which may have substituents, a heterocyclic group having 3 to 20 nuclear atoms which may have substituents, an aryl group having 6 to 40 nuclear carbon atoms which may have substituents, an aryloxyl group having 6 to 40 nuclear carbon atoms which may have substituents, an aralkyl group having 7 to 40 carbon atoms which may have substituents, an alkenyl group having 2 to 30 carbon atoms which may have substituents, an arylamino group 6 to 80 nuclear carbon atoms which may have substituents, an alkylamino group having 1 to 60 carbon atoms which may have substituents, an aralkylamino group having 7 to 80 carbon atoms which may have substituents, an alkylsilyl group having 1 to 30 carbon atoms which may have substituents, an arylsilyl group having 6 to 40 carbon atoms which may have substituents, a halogen atom, cyano group, nitro group, —S(R)O$_2$ or —S(R)O [R representing a substituent], and adjacent groups represented by R$^1$ to R$^8$ may be bonded to each other to form a cyclic structure.);

(c) A metal complex compound having a metal-carbene bond described in (a), wherein, in general formula (3) representing the partial structure represented by M(L$^2$)$_n$, at least one of L$^3$ and L$^4$ represents a partial structure represented by following general formula (5) or (6) or a limiting structure of resonance for the partial structure represented by general formula (5) or (6).

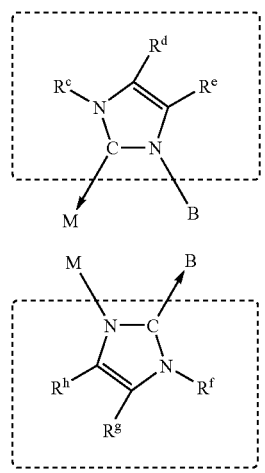

(5)

(6)

(an arrow in C (carbon atom)→M and C→B (boron atom) represents carbene bond, N represents nitrogen atom, R$^c$ to R$^h$ each independently represent hydrogen atom, an alkyl group having 1 to 50 carbon atoms which may have substituents, an alkenyl group having 2 to 50 carbon atoms which may have substituents, an aryl group having 6 to 50 nuclear carbon atoms which may have substituents or an aromatic heterocyclic group having 3 to 50 nuclear atoms which may have substituents, and adjacent groups may be bonded to each other to form a cyclic structure.);

(d) A metal complex compound having a metal-carbene bond described in (a) to (c), wherein M represents iridium atom;

(e) An electroluminescence device comprising an anode, a cathode and an organic thin film layer which comprises one layer or a plurality of layers comprising at least a light emitting layer and is disposed between the anode and the cathode, wherein at least one layer in the organic thin film layer comprises a metal complex compound having a metal-carbene bond described in (a) to (d);

(f) An electroluminescence device described in (e), wherein the light emitting layer comprises a metal complex compound having a metal-carbene bond described in (a) to (d) as a light emitting material;

(g) An electroluminescence device described in (e), wherein the light emitting layer comprises a metal complex compound having a metal-carbene bond described in (a) to (d) as a dopant;

(h) An electroluminescence device described in (e), wherein an electron injecting layer and/or an electron transporting layer is disposed between the light emitting layer and the cathode, and the electron injecting layer and/or the electron transporting layer comprises a π-electron-deficient heterocyclic derivative having nitrogen atom as a main component; and (i) An electroluminescence device described in (e), wherein a reducing dopant is added into an interfacial region of the cathode and the organic thin film layer.

The Effect of the Invention

The organic EL device using the metal complex compound of the present invention exhibits a great efficiency of light and has a long life. Moreover, the metal complex compound of the present invention facilitates the molecular design of the light emitting material for adjusting the color of emitted light.

BEST MODES FOR CARRYING OUT THE INVENTION

The metal complex compound of the present invention is a compound represented by the following general formula (1):

$$(L^1)_m M(L^2)_n \qquad (1)$$

In general formula (1) shown above, M represents iridium atom or platinum atom, L$^1$ and L$^2$ represent bidentate ligands different from each other, the partial structure represented by (L$^1$)$_m$M is represented by the following general formula (2), the partial structure represented by M(L$^2$)$_n$ is represented by the following general formula (3), m represents an integer of 0 to 2, n represents an integer of 1 to 3, and m+n represents a valence of the metal represented by M.

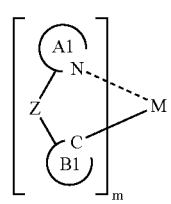

(2)

In general formula (2), N and C represent nitrogen atom and carbon atom, respectively, ring A1 represents an aromatic heterocyclic group having 3 to 50 nuclear atoms including nitrogen atom which may have substituents, ring B1 represents an aryl group having 6 to 50 nuclear carbon atoms which may have substituents, ring A1 and ring B1 are bonded with covalent bonds via Z, and Z may be bonded with any atom forming ring A1 and ring B1.

As the aromatic heterocyclic group having nitrogen atom represented by ring A1, groups having 3 to 20 nuclear atoms are preferable, and groups having 3 to 10 nuclear atoms are more preferable. Examples of the aromatic heterocyclic group having nitrogen atom include pyrazinyl group, pyridyl group, pyrimidyl group, pyrazolyl group, imidazolyl group, indolidinyl group, imidazopyridinyl group, quinolyl group, isoquinolyl group and quinoxalynyl group.

Among these groups, pyrazinyl group, pyridyl group, pyrimidinyl group, pyrazolyl group, imidazolyl group, quinolyl group and isoquinolyl group are preferable.

As the aryl group represented by ring B1, aryl groups having 6 to 40 nuclear carbon atoms are preferable, and aryl groups having 6 to 24 nuclear atoms are more preferable. Examples of the aryl group include phenyl group, 1-naphthyl group, 2-naphthyl group, 1-anthryl group, 2-anthryl group, 9-anthryl group, 1-phenanthryl group, 2-phenanthryl group, 3-phenanthryl group, 4-phenanthryl group, 9-phenanthryl group, 1-naphthacenyl group, 2-naphthacenyl group, 9-naphthacenyl group, 1-pyrenyl group, 2-pyrenyl group, 4-pyrenyl group, 2-biphenylyl group, 3-biphenylyl group, 4-biphenylyl group, p-terphenyl-4-yl group, p-terphenyl-3-yl group, p-terphenyl-2-yl group, m-terphenyl-4-yl group, m-terphenyl-3-yl group, m-terphenyl-2-yl group, o-tolyl group, m-tolyl group, p-tolyl group, p-t-butylphenyl group, p-(2-phenylpropyl)phenyl group, 3-methyl-2-naphthyl group, 4-methyl-1-naphthyl group, 4-methyl-1-anthryl group, 4'-methylbiphenylyl group, 4"-t-butyl-p-terphenyl -4-yl group, o-cumenyl group, m-cumenyl group, p-cumenyl group, 2,3-xylyl group, 3,4-xylyl group, 2,5-xylyl group and mesityl group.

Among these aryl groups, phenyl group, 1-naphthyl group, 2-naphthyl group, 9-phenanthryl group, 2-biphenylyl group, 3-biphenylyl group, 4-biphenylyl group, p-tolyl group and 3,4-xylyl group are more preferable.

In general formula (2), Z represents a single bond, —O—, —S—, —CO—, —(CR'R")$_a$—, —(SiR'R")$_a$— or —NR'—. R' and R" each independently represent hydrogen atom, an aryl group having 6 to 50 nuclear carbon atoms which may have substituents, an aromatic heterocyclic group having 3 to 50 nuclear atoms which may have substituents or an alkyl group having 1 to 50 carbon atoms which may have substituents. a represents an integer of 1 to 10, and the atoms and the groups represented by R' and R" may be the same with or different from each other.

Examples of the aryl group represented by R' and R" include the groups described as the examples of the aryl group represented by ring B1. Examples of the aromatic heterocyclic group represented by R' and R" include the groups described as the examples of the aromatic heterocyclic group represented by ring A1. Examples of the alkyl group represented by R' and R" are shown in the following.

Preferable examples of the alkyl group represented by R' and R" include alkyl groups having 1 to 10 carbon atoms, such as methyl group, ethyl group, propyl group, isopropyl group, n-butyl group, s-butyl group, isobutyl group, t-butyl group, n-pentyl group, n-hexyl group, n-heptyl group, n-octyl group, n-nonyl group, n-decyl group, n-undecyl group, n-dodecyl group, n-tridecyl group, n-tetradecyl group, n-pentadecyl group, n-hexadecyl group, n-heptadecyl group, n-octadecyl group, neopentyl group, 1-methylpentyl group, 2-methylpentyl group, 1-pentylhexyl group, 1-butylpentyl group, 1-heptyloctyl group, 3-methylpentyl group, hydroxymethyl group, 1-hydroxyethyl group, 2-hydroxyethyl group, 2-hydroxyisobutyl group, 1,2-dihydroxyethyl group, 1,3-dihydroxyisopropyl group, 2,3-dihydroxy-t-butyl group, 1,2,3-trihydroxypropyl group, aminomethyl group, 1-aminoethyl group, 2-aminoethyl group, 2-aminoisobutyl group, 1,2-diaminoethyl group, 1,3-diaminoisopropyl group, 2,3-diamino-t-butyl group, 1,2,3-triaminopropyl group, cyanomethyl group, 1-cyanoethyl group, 2-cyanoethyl group, 2-cyanoisobutyl group, 1,2-dicyanoethyl group, 1,3-dicyanoisopropyl group, 2,3-dicyano-t-butyl group, 1,2,3- tricyanopropyl group, nitromethyl group, 1-nitroethyl group, 2-nitroethyl group, 2-nitroisobutyl group, 1,2-dinitroethyl group, 2,3-dinitro-t-butyl group, 1,2,3-trinitropropyl group, cyclopentyl group, cyclohexyl group, cyclooctyl group, 3,5-dimethyl-cyclohexyl group and 3,3,5,5-tetramethyl-cyclohexyl group.

Among these alkyl groups, methyl group, ethyl group, propyl group, isopropyl group, n-butyl group, s-butyl group, isobutyl group, t-butyl group, n-pentyl group, n-hexyl group, n-heptyl group, n-octyl group, n-nonyl group, n-decyl group, n-undecyl group, n-dodecyl group, n-tridecyl group, n-tetradecyl group, n-pentadecyl group, n-hexadecyl group, n-heptadecyl group, n-octadecyl group, neopentyl group, 1-methylpentyl group, 1-pentylhexyl group, 1-butylpentyl group, 1-heptyloctyl group, cyclohexyl group, cyclooctyl group, 3,5-dimethylcyclohexyl group and 3,3,5,5-tetramethylcyclohexyl group are preferable.

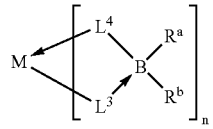

(3)

In general formula (3), B represents boron atom, $L^3$ and $L^4$ each represent a crosslinking group having a covalent bond (shown by a solid line) and a coordinate bond (shown by an arrow), at least one of $L^3$ and $L^4$ represents an aromatic heterocyclic group having 3 to 50 nuclear atoms and nitrogen atom which has a coordinate bond with carbene carbon atom and may have substituents, $R^a$ and $R^b$ each independently represent hydrogen atom, an alkyl group having 1 to 50 carbon atoms which may have substituents, an alkenyl group having 2 to 50 carbon atoms which may have substituents, an aryl group having 6 to 50 nuclear carbon atoms which may have substituents or an aromatic heterocyclic group having 3 to 50 nuclear atoms which may have substituents, and groups represented by $L^3$, $L^4$, $R^a$ and $R^b$ may be bonded to each other to form a cyclic structure.

Examples of the aromatic heterocyclic group having 3 to 50 nuclear atoms and nitrogen atom which is represented by $L^3$ and $L^4$ in general formula (3) include 1-(imidazol-2-ylidene) group, 1-(4,5-benzimidazol-2-ylidene) group, 3-(imidazo[1,5a]pyridin-2-ylidene) group, 1-(1,3,4-triazol-2-ylidene) group, 1-(1,2,4-triazol-5-ylidene) group, 1-(1,2,3,4-tetrazol-5-ylidene) group, 1-(pyrazole-$N^2$) group, 1-(4,5-benzopyrazole-$N^2$) group, 1-(3,4-benzopyrazole-$N^2$) group, 1-(4,5-benzo-1,2,3-triazole-$N^2$) group, 2-(4,5-benzo-1,2,3-triazole-$N^3$) group, 1-(1,2,4-triazole-$N^2$) group, 1-(1,2,3,4-tetrazole-$N^2$) group and 2-(1,2,3,4-tetrazole-$N^3$) group. The above aromatic heterocyclic group may be a limiting structure of resonance for these structures.

Specific examples of the group represented by $L^3$ and $L^4$ include compounds represented by the following structural formulae, substituted compounds obtained from these compounds and compounds having a limiting structure of resonance for these structures.

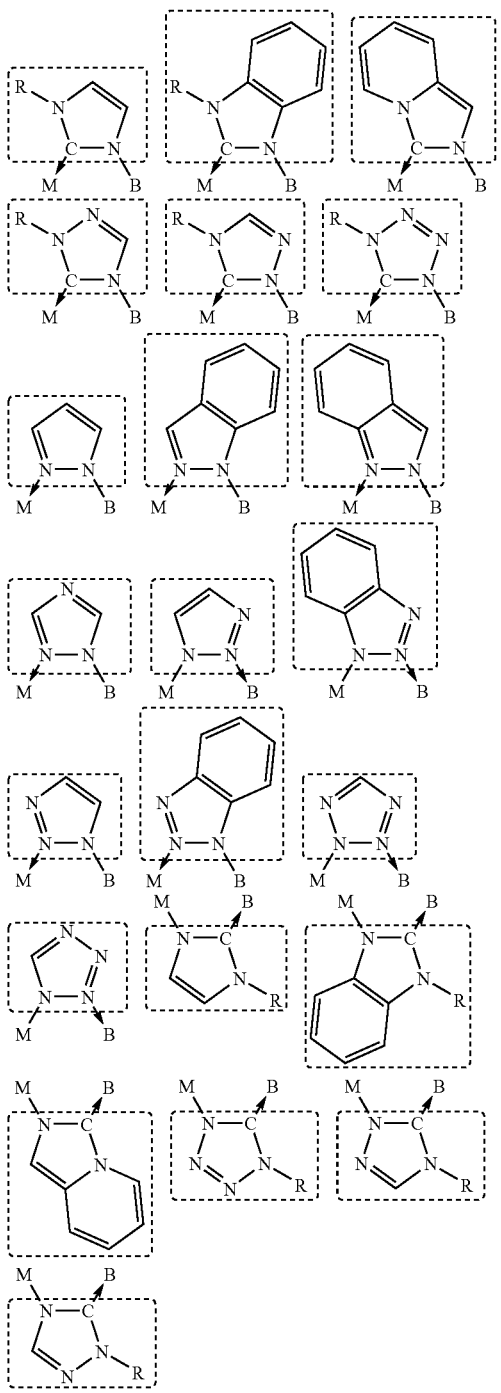

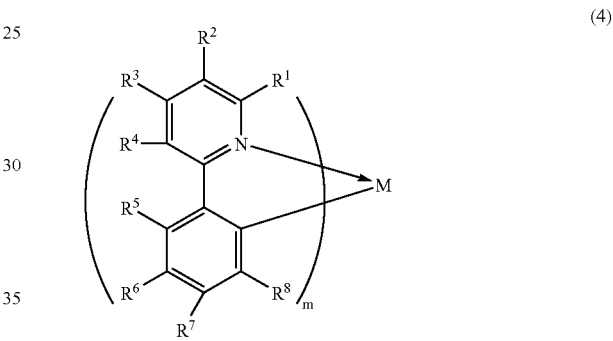

(4)

Examples of the alkyl group and aryl group which are represented by $R^a$ and $R^b$ in general formula (3) include the groups described above as the examples of the group represented by R' and R" in general formula (2). Methyl group, ethyl group, phenyl group and phenyl group substituted with a halogen atom are preferable.

As the alkenyl group represented by $R^a$ and $R^b$, alkenyl groups having 2 to 30 carbon atoms are preferable, and alkenyl groups having 2 to 16 carbon atoms are more preferable. Examples of the alkenyl group include vinyl group, allyl group, 1-butenyl group, 2-butenyl group, 3-butenyl group, 1,3-butadienyl group, 1-methylvinyl group, styryl group, 1,2-diphenylvinyl group, 2,2-diphenylvinyl group, 1-methylallyl group, 1,1-dimethylallyl group, 2-methylallyl group, 1-phenylallyl group, 2-phenylallyl group, 3-phenylallyl group, 3,3-diphenylallyl group, 1,2-dimethylallyl group, 1-phenyl-1-butenyl group and 3-phenyl-1-butenyl group. Among these groups, styryl group, 2,2-diphenylvinyl group and 1,2-diphenylvinyl group are preferable.

Examples of the aromatic heterocyclic group having 3 to 50 nuclear atoms which may have substituents, which is represented by $R^a$ and $R^b$, include 1-pyrazole group, 1-(4,5-benzopyrazole) group, 1-(3,4-benzo-pyrazole) group, 1-(4,5-benzo-1,2,3-triazole) group, 2-(4,5-benzo-1,2,3-triazole) group, 1-(1,2,3-triazole) group, 1-(1,2,4-triazole) group, 1-(1,2,3,4-tetrazole) group and 2-(1,2,3,4-tetrazole) group. Among these groups, 1-pyrazole group, 1-(1,2,3-triazole) group and 1-(1,2,4-triazole) group are preferable.

In the present invention, it is preferable that the partial structure represented by $(L^1)_mM$ which is represented by the above general formula (2) is a partial structure represented by the following general formula (4), and m represents 2.

In general formula (4), $R^1$ to $R^8$ each independently represent hydrogen atom, an alkyl group having 1 to 30 carbon atoms which may have substituents, a halogenated alkyl group having 1 to 30 carbon atoms which may have substituents, an alkoxyl group having 1 to 30 carbon atoms which may have substituents, a heterocyclic group having 3 to 20 nuclear atoms which may have substituents, an aryl group having 6 to 40 nuclear carbon atoms which may have substituents, an aryloxyl group having 6 to 40 nuclear carbon atoms which may have substituents, an aralkyl group having 7 to 40 carbon atoms which may have substituents, an alkenyl group having 2 to 30 carbon atoms which may have substituents, an arylamino group 6 to 80 nuclear carbon atoms which may have substituents, an alkylamino group having 1 to 60 carbon atoms which may have substituents, an aralkylamino group having 7 to 80 carbon atoms which may have substituents, an alkylsilyl group having 1 to 30 carbon atoms which may have substituents, an arylsilyl group having 6 to 40 carbon atoms which may have substituents, a halogen atom, cyano group, nitro group, —S(R)O$_2$ or —S(R)O [R representing a substituent], and adjacent groups represented by $R^1$ to $R^8$ may be bonded to each other to form a cyclic structure.

As the alkyl group represented by $R^1$ to $R^8$, alkyl groups having 1 to 10 carbon atoms are preferable. Examples of the alkyl group include methyl group, ethyl group, propyl group, isopropyl group, n-butyl group, s-butyl group, isobutyl group, t-butyl group, n-pentyl group, n-hexyl group, n-heptyl group, n-octyl group, n-nonyl group, n-decyl group, n-undecyl group, n-dodecyl group, n-tridecyl group, n-tetradecyl group, n-pentadecyl group, n-hexadecyl group, n-heptadecyl group, n-octadecyl group, neopentyl group, 1-methylpentyl group, 2-methylpentyl group, 1-pentylhexyl group, 1-butylpentyl group, 1-heptyloctyl group, 3-methylpentyl group, hydroxymethyl group, 1-hydroxyethyl group, 2-hydroxyethyl group, 2-hydroxyisobutyl group, 1,2-dihydroxyethyl group, 1,3-dihydroxyisopropyl group, 2,3-dihydroxy-t-butyl group, 1,2,3-tri-hydroxypropyl group, aminomethyl group, 1-aminoethyl group, 2-aminoethyl group, 2-aminoisobutyl group, 1,2-diaminoethyl group, 1,3-diaminoisopropyl group, 2,3-diamino-t-butyl group, 1,2,3-triamino-propyl group, cyanomethyl group, 1-cyanoethyl group, 2-cyanoethyl group, 2-cyanoisobutyl group, 1,2-dicyanoethyl group, 1,3-dicyanoisopropyl group, 2,3-dicyano-t-butyl group, 1,2,3-tricyanopropyl group, nitromethyl group, 1-nitroethyl group, 2-nitroethyl group, 1,2-dinitroethyl group, 2,3-dinitro-t-butyl group, 1,2,3-trinitropropyl group, cyclopentyl group, cyclohexyl group, cyclooctyl group, 3,5-dimethylcyclohexyl group and 3,3,5,5-tetramethyl-cyclohexyl group.

Among these alkyl groups, methyl group, ethyl group, propyl group, isopropyl group, n-butyl group, s-butyl group, isobutyl group, t-butyl group, n-pentyl group, n-hexyl group, n-heptyl group, n-octyl group, n-nonyl group, n-decyl group, n-undecyl group, n-dodecyl group, n-tridecyl group, n-tetradecyl group, n-pentadecyl group, n-hexadecyl group, n-heptadecyl group, n-octadecyl group, neopentyl group, 1-methylpentyl group, 1-pentylhexyl group, 1-butylpentyl group, 1-heptyloctyl group, cyclohexyl group, cyclooctyl group, 3,5-dimethylcyclohexyl group and 3,3,5,5-tetramethylcyclohexyl group are more preferable.

As the halogenated alkyl group represented by $R^1$ to $R^8$, halogenated alkyl groups having 1 to 10 carbon atoms are preferable. Examples of the halogenated alkyl group include chloromethyl group, 1-chloroethyl group, 2-chloroethyl group, 2-chloroisobutyl group, 1,2-dichloroethyl group, 1,3-dichloroisopropyl group, 2,3-dichloro-t-butyl group, 1,2,3-trichloropropyl group, bromomethyl group, 1-bromoethyl group, 2-bromoethyl group, 2-bromoisobutyl group, 1,2-dibromoethyl group, 1,3-dibromoisopropyl group, 2,3-dibromo-t-butyl group, 1,2,3-tribromopropyl group, iodomethyl group, 1-iodoethyl group, 2-iodoethyl group, 2-iodoisobutyl group, 1,2-diiodoethyl group, 1,3-diiodoisopropyl group, 2,3-diiodo-t-butyl group, 1,2,3-triiodopropyl group, fluoromethyl group, 1-fluoroethyl group, 2-fluoroethyl group, 2-fluoroisobutyl group, 1,2-difluoroethyl group, 1,3-difluoromethyl group, trifluoromethyl group, pentafluoroethyl group, perfluoroisopropyl group, perfluorobutyl group and perfluorocyclohexyl group.

Among these halogenated alkyl groups, fluoromethyl group, trifluoromethyl group, pentafluoroethyl group, perfluoroisopropyl group, perfluorobutyl group and perfluorocyclohexyl group are more preferable.

The alkoxyl group represented by $R^1$ to $R^8$ is a group represented by —$OX^1$. Examples of the group represented by $X^1$ include the groups described above as the examples of the alkyl group and the halogenated alkyl group.

As the heterocyclic group represented by $R^1$ to $R^8$, heterocyclic groups having 3 to 10 nuclear atoms are preferable. Examples of the heterocyclic group include 1-pyrrolyl group, 2-pyrrolyl group, 3-pyrrolyl group, pyrazinyl group, 2-pyridinyl group, 1-imidazolyl group, 2-imidazolyl group, 1-pyrazolyl group, 1-indolidinyl group, 2-indolidinyl group, 3-indolidinyl group, 5-indolidinyl group, 6-indolidinyl group, 7-indolidinyl group, 8-indolidinyl group, 2-imidazopyridinyl group, 3-imidazopyridinyl group, 5-imidazopyridinyl group, 6-imidazopyridinyl group, 7-imidazopyridinyl group, 8-imidazopyridinyl group, 3-pyridinyl group, 4-pyridinyl group, 1-indolyl group, 2-indolyl group, 3-indolyl group, 4-indolyl group, 5-indolyl group, 6-indolyl group, 7-indolyl group, 1-isoindolyl group, 2-isoindolyl group, 3-isoindolyl group, 4-isoindolyl group, 5-isoindolyl group, 6-isoindolyl group, 7-isoindolyl group, 2-furyl group, 3-furyl group, 2-benzofuranyl group, 3-benzofuranyl group, 4-benzofuranyl group, 5-benzofuranyl group, 6-benzofuranyl group, 7-benzofuranyl group, 1-isobenzofuranyl group, 3-isobenzofuranyl group, 4-isobenzofuranyl group, 5-isobenzofuranyl group, 6-isobenzofuranyl group, 7-isobenzofuranyl group, 2-quinolyl group, 3-quinolyl group, 4-quinolyl group, 5-quinolyl group, 6-quinolyl group, 7-quinolyl group, 8-quinolyl group, 1-isoquinolyl group, 3-isoquinolyl group, 4-isoquinolyl group, 5-isoquinolyl group, 6-isoquinolyl group, 7-isoquinolyl group, 8-isoquinolyl group, 2-quinoxanyl group, 5-quinoxanyl group, 6-quinoxanyl group, 1-carbazolyl group, 2-carbazolyl group, 3-carbazolyl group, 4-carbazolyl group, 9-carbazolyl group, β-carbolin-1-yl, β-carbolin-3-yl, β-carbolin-4-yl, β-carbolin-5-yl, β-carbolin-6-yl, β-carbolin-7-yl, β-carbolin-8-yl, β-carbolin-9-yl, 1-phenanthridinyl group, 2-phenanthridinyl group, 3-phenanthridinyl group, 4-phenanthridinyl group, 6-phenanthridinyl group, 7-phenanthridinyl group, 8-phenanthridinyl group, 9-phenanthridinyl group, 10-phenanthridinyl group, 1-acridinyl group, 2-acridinyl group, 3-acridinyl group, 4-acridinyl group, 9-acridinyl group, 1,7-phenanthrolin-2-yl group, 1,7-phenanthrolin-3-yl group, 1,7-phenanthrolin-4-yl group, 1,7-phenanthrolin-5-yl group, 1,7-phenanthrolin-6-yl group, 1,7-phenanthrolin-8-yl group, 1,7-phenanthrolin-9-yl group, 1,7-phenanthrolin-10-yl group, 1,8-phenanthrolin-2-yl group, 1,8-phenanthrolin-3-yl group, 1,8-phenanthrolin-4-yl group, 1,8-phenanthrolin-5-yl group, 1,8-phenanthrolin-6-yl group, 1,8-phenanthrolin-7-yl group, 1,8-phenanthrolin-9-yl group, 1,8-phenanthrolin-10-yl group, 1,9-phenanthrolin-2-yl group, 1,9-phenanthrolin-3-yl group, 1,9-phenanthrolin-4-yl group, 1,9-phenanthrolin-5-yl group, 1,9-phenanthrolin-6-yl group, 1,9-phenanthrolin-7-yl group, 1,9-phenanthrolin-8-yl group, 1,9-phenanthrolin-10-yl group, 1,10-phenanthrolin-2-yl group, 1,10-phenanthrolin-3-yl group, 1,10-phenanthrolin-4-yl group, 1,10-phenanthrolin-5-yl group, 2,9-phenanthrolin-1-yl group, 2,9-phenanthrolin-3-yl group, 2,9-phenanthrolin-4-yl group, 2,9-phenanthrolin-5-yl group, 2,9-phenanthrolin-6-yl group, 2,9-phenanthrolin-7-yl group, 2,9-phenanthrolin-8-yl group, 2,9-phenanthrolin-10-yl group, 2,8-phenanthrolin-1-yl group, 2,8-phenanthrolin-3-yl group, 2,8-phenanthrolin-4-yl group, 2,8-phenanthrolin-5-yl group, 2,8-phenanthrolin-6-yl group, 2,8-phenanthrolin-7-yl group, 2,8-phenanthrolin-9-yl group, 2,8-phenanthrolin-10-yl group, 2,7-phenanthrolin-1-yl group, 2,7-phenanthrolin-3-yl group, 2,7-phenanthrolin-4-yl group, 2,7-phenanthrolin-5-yl group, 2,7-phenanthrolin-6-yl group, 2,7-phenanthrolin-8-yl group, 2,7-phenanthrolin-9-yl group, 2,7-phenanthrolin-10-yl group, 1-phenazinyl group, 2-phenazinyl group, 1-phenothiazinyl group, 2-phenothiazinyl group, 3-phenothiazinyl group, 4-phenothiazinyl group, 10-phenothiazinyl group, 1-phenoxazinyl group, 2-phenoxazinyl group, 3-phenoxazinyl group, 4-phenoxazinyl group, 10-phenoxazinyl group, 2-oxazolyl group, 4-oxazolyl group, 5-oxazolyl group, 2-oxadiazolyl group, 5-oxadiazolyl group, 3-furazanyl group, 2-thienyl group, 3-thienyl group, 2-methylpyrrol-1-yl group, 2-methylpyrrol-3-yl group, 2-methylpyrrol-4-yl group, 2-methyl-pyrrol-5-yl group, 3-methylpyrrol-1-yl group, 3-methylpyrrol-2-yl group, 3-methylpyrrol-4-yl group, 3-methylpyrrol-5-yl group, 2-t-butylpyrrol-4-yl group, 3-(2-phenylpropyl)pyrrol-1-yl group, 2-methyl-1-indolyl group, 4-methyl-1-indolyl group, 2-methyl-3-indolyl group, 4-methyl-3-indolyl group, 2-t-butyl-1-indolyl group, 4-t-butyl-1-indolyl group, 2-t-butyl-3-indolyl group and 4-t-butyl-3-indolyl group.

Among these heterocyclic groups, 2-pyridinyl group, 1-indolidinyl group, 2-indolidinyl group, 3-indolidinyl group, 5-indolidinyl group, 6-indolidinyl group, 7-indolidinyl group, 8-indolidinyl group, 2-imidazopyridinyl group, 3-imidazopyridinyl group, 5-imidazopyridinyl group, 6-imidazopyridinyl group, 7-imidazopyridinyl group, 8-imidazopyridinyl group, 3-pyridinyl group, 4-pyridinyl group, 1-indolyl group, 2-indolyl group, 3-indolyl group, 4-indolyl group, 5-indolyl group, 6-indolyl group, 7-indolyl group, 1-isoindolyl group, 2-isoindolyl group, 3-isoindolyl group, 4-isoindolyl group, 5-isoindolyl group, 6-isoindolyl group, 7-isoindolyl group, 1-carbazolyl group, 2-carbazolyl group, 3-carbazolyl group, 4-carbazolyl group and 9-carbazolyl group are preferable.

As the aryl group represented by $R^1$ to $R^8$, aryl groups having 6 to 24 nuclear carbon atoms are preferable. Examples of the aryl group include phenyl group, 1-naphthyl group, 2-naphthyl group, 1-anthryl group, 2-anthryl group, 9-anthryl group, 1-phenanthryl group, 2-phenanthryl group, 3-phenanthryl group, 4-phenanthryl group, 9-phenanthryl group, 1-naphthacenyl group, 2-naphthacenyl group, 9-naphthacenyl group, 1-pyrenyl group, 2-pyrenyl group, 4-pyrenyl group, 2-biphenylyl group, 3-biphenylyl group, 4-biphenylyl group, p-terphenyl-4-yl group, p-terphenyl-3-yl group, p-terphenyl-2-yl group, m-terphenyl-4-yl group, m-terphenyl-3-yl group, m-terphenyl-2-yl group, o-tolyl group, m-tolyl group, p-tolyl group, p-t-butylphenyl group, p-(2-phenylpropyl)phenyl group, 3-methyl-2-naphthyl group, 4-methyl-1-naphthyl group, 4-methyl-1-anthryl group, 4'-methylbiphenylyl group, 4"-t-butyl-p-terphenyl-4-yl group, o-cumenyl group, m-cumenyl group, p-cumenyl group, 2,3-xylyl group, 3,4-xylyl group, 2,5-xylyl group, mesityl group and perfluorophenyl group.

Among these aryl groups, phenyl group, 1-naphthyl group, 2-naphthyl group, 9-phenanthryl group, 2-biphenylyl group, 3-biphenylyl group, 4-biphenylyl group, p-tolyl group and 3,4-xylyl group are more preferable.

The aryloxyl group represented by $R^1$ to $R^8$ is a group represented by —OAr. Examples of the group represented by Ar include the groups described above as the examples of the aryl group.

As the aralkyl group represented by $R^1$ to $R^8$, aralkyl groups having 7 to 18 carbon atoms are preferable. Examples of the aralkyl group include benzyl group, 1-phenylethyl group, 2-phenylethyl group, 1-phenylisopropyl group, 2-phenylisopropyl group, phenyl-t-butyl group, α-naphthylmethyl group, 1-α-naphthylethyl group, 2-α-naphthylethyl group, 1-α-naphthylisopropyl group, 2-α-naphthylisopropyl group, β-naphthylmethyl group, 1-β-naphthylethyl group, 2-β-naphthylethyl group, 1-β-naphthylisopropyl group, 2-β-naphthylisopropyl group, 1-pyrrolylmethyl group, 2-(1-pyrrolyl)ethyl group, p-methylbenzyl group, m-methylbenzyl group, o-methylbenzyl group, p-chlorobenzyl group, m-chlorobenzyl group, o-chlorobenzyl group, p-bromobenzyl group, m-bromobenzyl group, o-bromobenzyl group, p-iodobenzyl group, m-iodobenzyl group, o-iodobenzyl group, p-hydroxybenzyl group, m-hydroxybenzyl group, o-hydroxybenzyl group, p-aminobenzyl group, m-aminobenzyl group, o-aminobenzyl group, p-nitrobenzyl group, m-nitrobenzyl group, o-nitrobenzyl group, p-cyanobenzyl group, m-cyanobenzyl group, o-cyanobenzyl group, 1-hydroxy-2-phenylisopropyl group and 1-chloro-2-phenylisopropyl group. Among these aralkyl groups, benzyl group, p-cyanobenzyl group, m-cyanobenzyl group, o-cyanobenzyl group, 1-phenylethyl group, 2-phenylethyl group, 1-phenylisopropyl group and 2-phenylisopropyl groups are more preferable.

As the alkenyl group represented by $R^1$ to $R^8$, alkenyl groups having 2 to 16 carbon atoms are preferable. Examples of the alkenyl group include vinyl group, allyl group, 1-butenyl group, 2-butenyl group, 3-butenyl group, 1,3-butadienyl group, 1-methylvinyl group, styryl group, 2,2-diphenylvinyl group, 1,2-diphenylvinyl group, 1-methylallyl group, 1,1-dimethylallyl group, 2-methylallyl group, 1-phenylallyl group, 2-phenylallyl group, 3-phenylallyl group, 3,3-diphenylallyl group, 1,2-dimethylallyl group, 1-phenyl-1-butenyl group and 3-phenyl-1-butenyl group. Among these alkenyl groups, styryl group, 2,2-diphenylvinyl group and 1,2-diphenylvinyl group are more preferable.

The arylamino group, the alkylamino group and the aralkylamino group represented by $R^1$ to $R^8$ are represented by —$NQ^1Q^2$. It is preferable that $Q^1$ and $Q^2$ each independently represent an atom or a group having 1 to 20 carbon atoms. Examples of the atoms and the group having 1 to 20 carbon atoms include hydrogen atom and the groups described above as the examples of the aryl group, the alkyl group and the aralkyl group.

Examples of the alkylsilyl group represented by $R^1$ to $R^8$ include trimethylsilyl group, triethylsilyl group, t-butyldimethylsilyl group, vinyldimethylsilyl group and propyldimethylsilyl group.

Examples of the aryl silyl group represented by $R^1$ to $R^8$ include triphenylsilyl group, phenyldimethylsilyl group and t-butyldiphenylsilyl group.

Examples of the halogen atom represented by $R^1$ to $R^8$ include fluorine atom, chlorine atom, bromine atom and iodine atom.

Examples of the substituent represented by $R^0$ in the groups represented by —$S(R^0)O_2$ and —$S(R^0)O$ which are the groups represented by $R^1$ to $R^8$ include the groups described above as the examples of the groups represented by $R^1$ to $R^8$.

Examples of the cyclic structure which may be formed by bonding of the groups represented by $R^1$ to $R^8$ with each other include structures of cycloalkanes having 4 to 12 carbon atoms such as cyclobutane, cyclopentane, cyclohexane, adamantane and norbornane, structures of cycloalkenes having 4 to 12 carbon atoms such as cyclobutene, cyclopentene, cyclohexene, cycloheptene and cyclooctene, structures of cycloalkadienes having 6 to 12 carbon atoms such as cyclohexadiene, cycloheptadiene and cyclooctadiene, and aromatic rings having 6 to 50 carbon atoms such as benzene ring, naphthalene ring, phenanthrene ring, anthracene ring, pyrene ring, chrysene ring and acenaphthylene ring.

In the present invention, in general formula (3) representing the partial structure represented by $M(L^2)_n$ in general formula (1), at least one of $L^3$ and $L^4$ represents a partial structure represented by the following general formula (5) or (6) or a limiting structure of resonance for the partial structure represented by general formula (5) or (6).

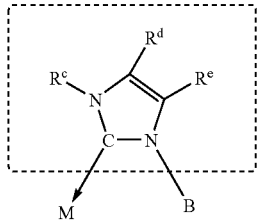

(5)

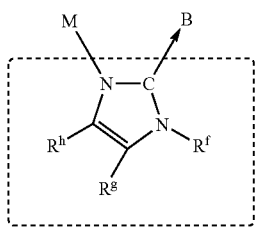

(6)

The arrow in C (carbon atom)→M and C→B (boron atom) represents carbene bonds, N represents nitrogen atom, $R^c$ to $R^h$ each independently represent hydrogen atom, an alkyl group having 1 to 50 carbon atoms which may have substituents, an alkenyl group having 2 to 50 carbon atoms which may have substituents, an aryl group having 6 to 50 nuclear carbon atoms which may have substituents or an aromatic heterocyclic group having 3 to 50 nuclear atoms which may have substituents, and adjacent groups may be bonded to each other to form a cyclic structure.

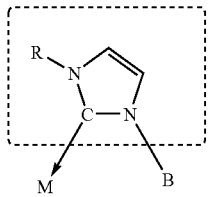

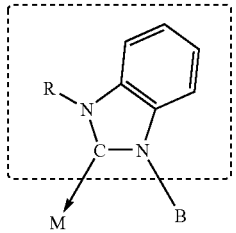

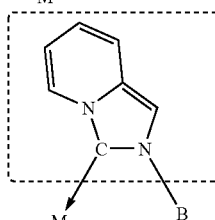

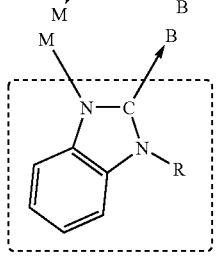

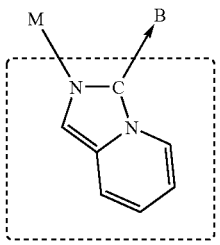

-continued

Examples of the alkyl group having 1 to 50 carbon atoms which may have substituents, the alkenyl group having 2 to 50 carbon atoms which may have substituents, the aryl group having 6 to 50 nuclear carbon atoms which may have substituents and the aromatic heterocyclic group having 3 to 50 nuclear atoms which may have substituents, which are represented by $R^c$ to $R^h$, include the groups described as the examples of the corresponding groups represented by $R^1$ to $R^8$.

Specific examples of the cyclic structure formed by bonding the groups represented by $L^3$, $L^4$, $R^a$ and $R^b$ in general formula (3) to each other include structures shown in the following:

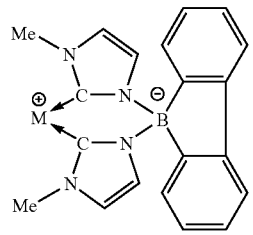

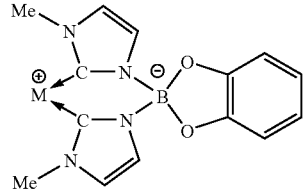

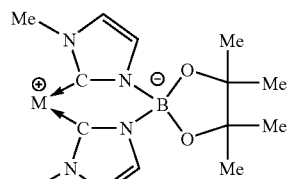

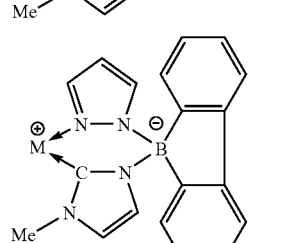

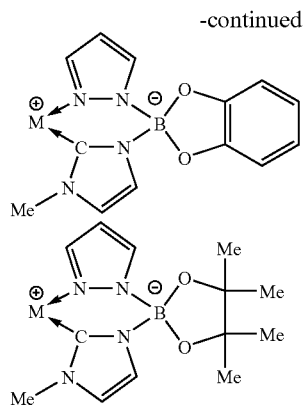

Examples of the metal complex compound of the present invention which is represented by general formula (1) are shown in the following. Derivatives of the compounds shown as the examples are also included in the present invention. The metal complex compound is not limited to the compounds shown as the examples. The compounds shown as the examples are exhibited as intramolecular ionic complexes. However, compounds having resonance structures of the exhibited structures are also included. Taking a metal complex compound of the present invention as an example, it is shown that, as the limiting structure of resonance for the metal complex compound, extremely numerous structures can exist, representative examples of which are shown in the following.

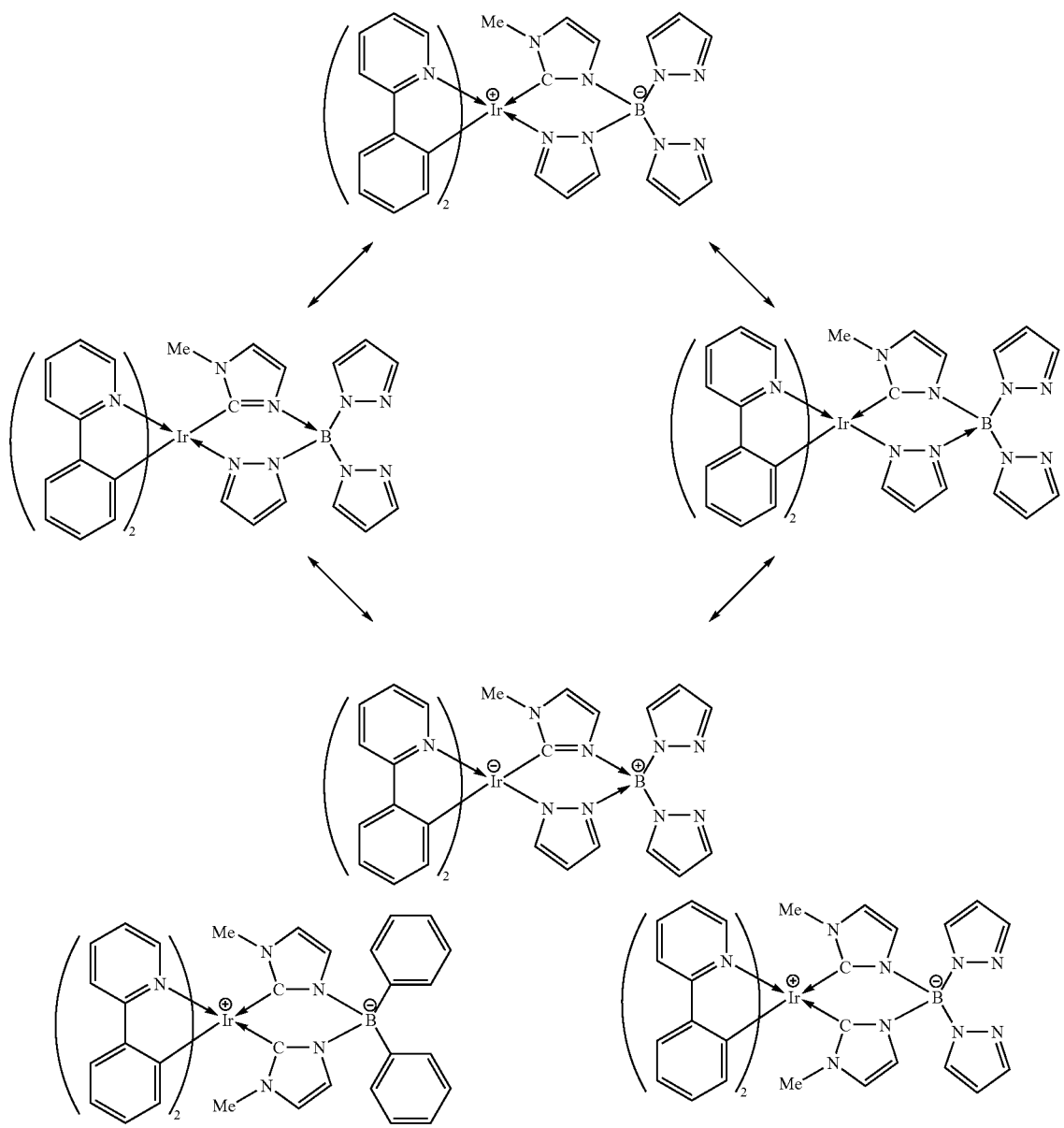

-continued
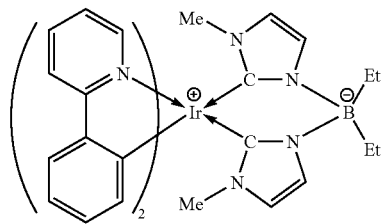
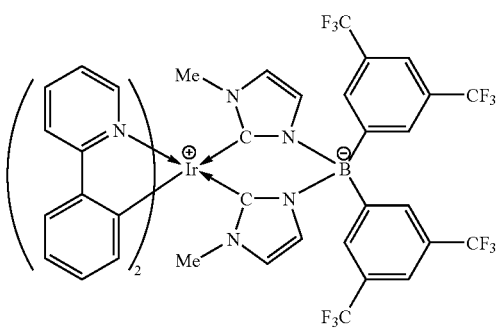
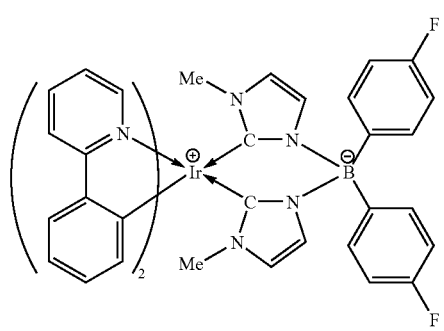
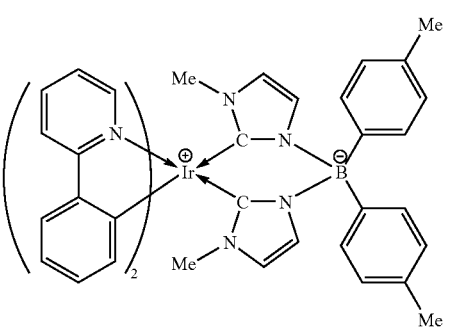
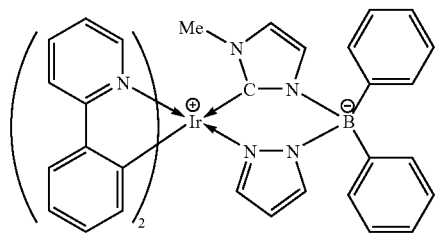
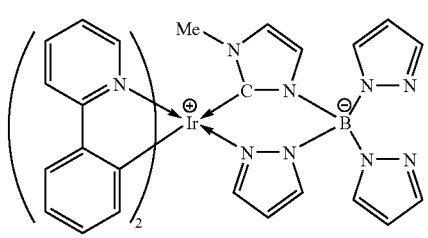
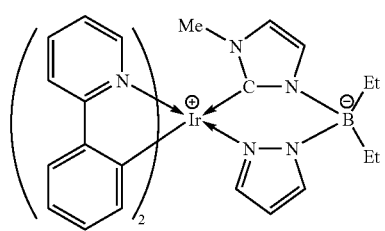
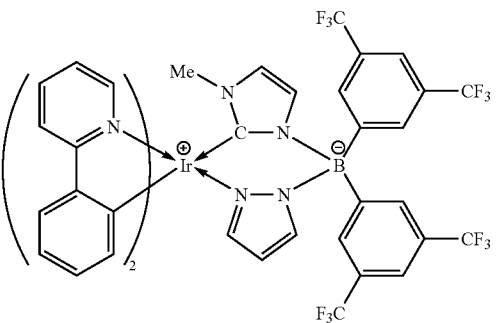
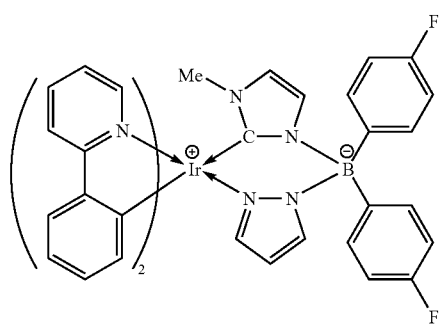
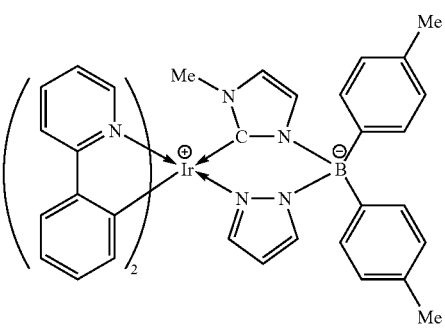

-continued
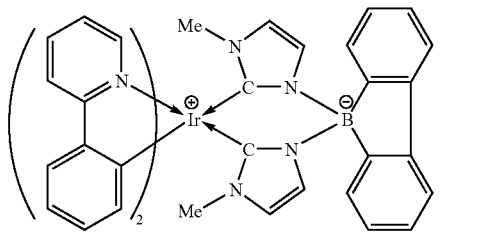
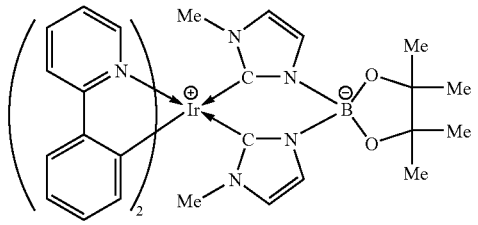
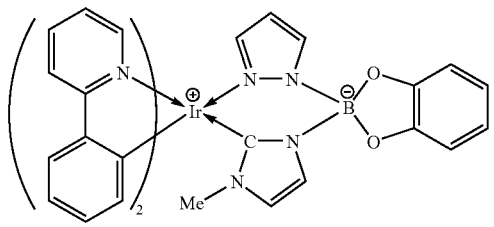
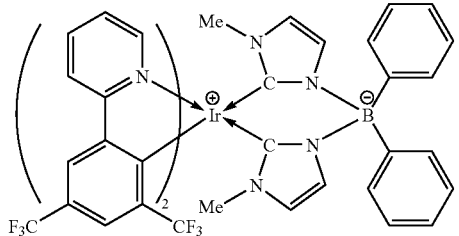
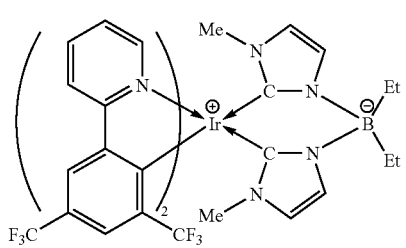
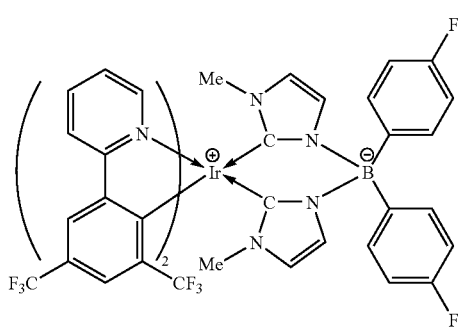
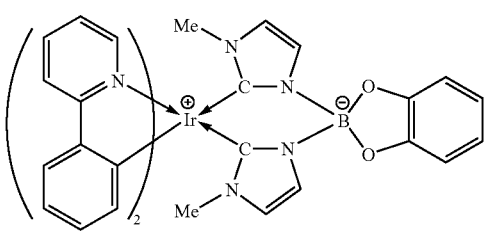
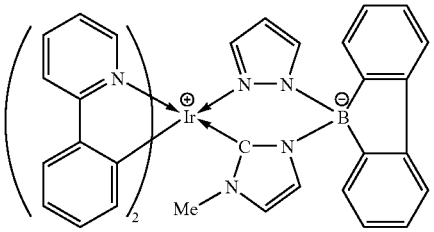
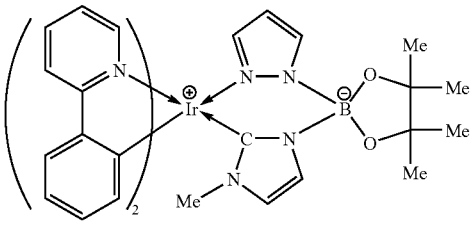
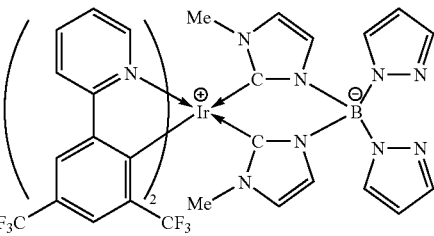
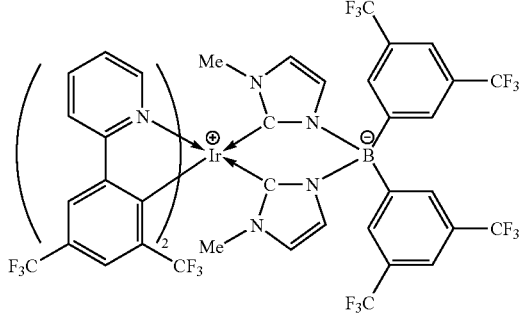
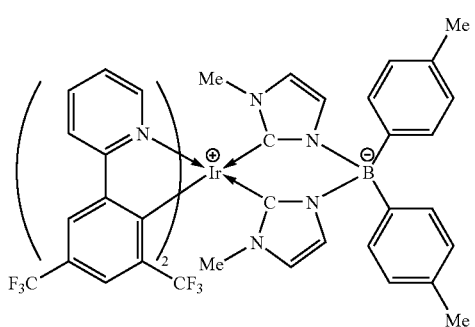

-continued
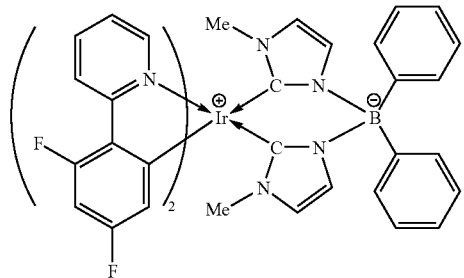
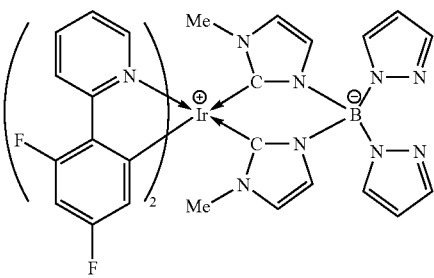
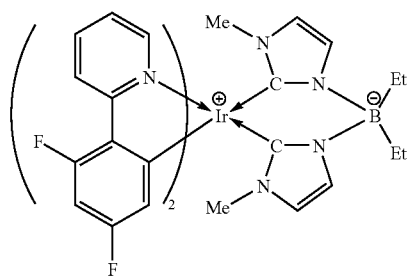
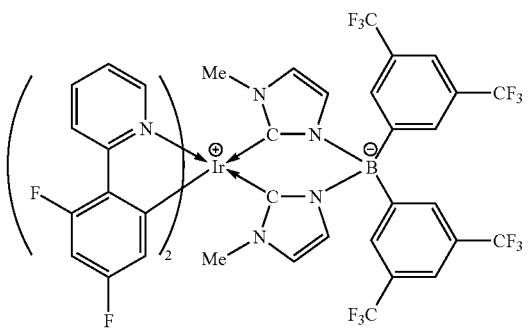
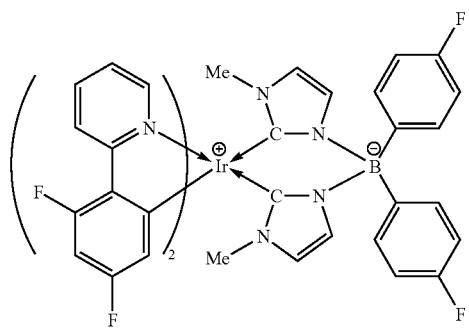
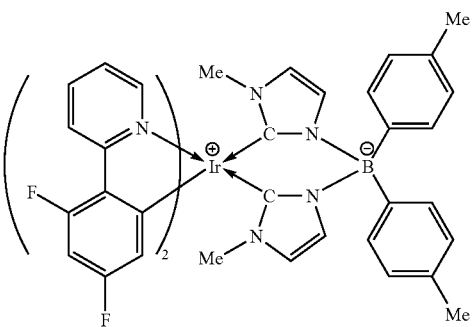
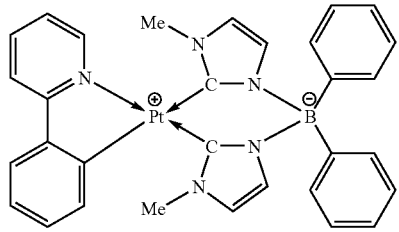
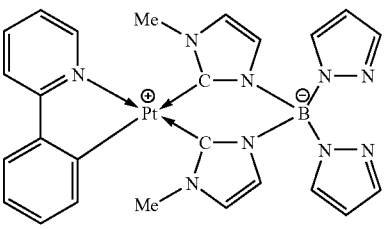
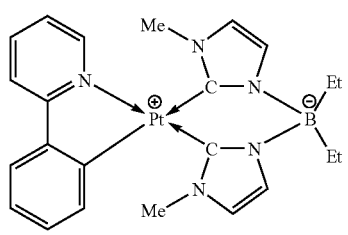
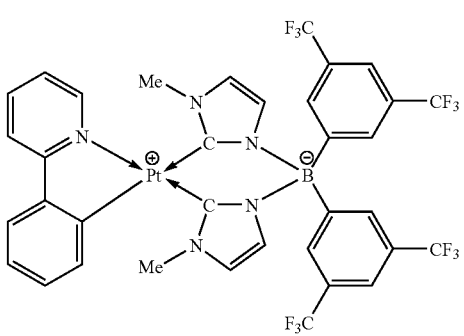

-continued

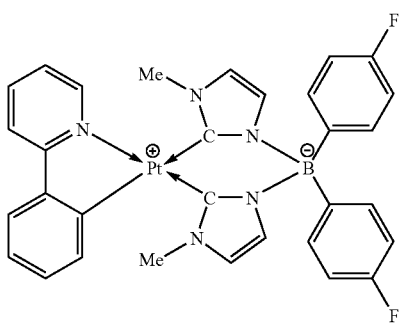

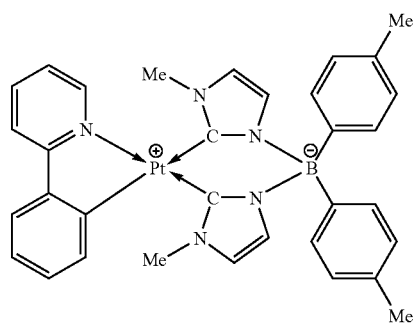

The organic EL device of the present invention comprises an anode, a cathode and an organic thin film layer which comprises one layer or a plurality of layers comprising at least a light emitting layer and is disposed between the anode and the cathode, wherein at least one layer in the organic thin film layer comprises the metal complex compound of the present invention.

The content of the metal complex compound of the present invention in the above organic thin film layer is, in general, 0.1 to 100% by weight and preferably 1 to 30% by weight based on the entire amount by mass of the present invention.

In the organic EL device of the present invention, it is preferable that the light emitting layer comprises a metal complex compound of the present invention as the light emitting material. In general, the light emitting layer is formed as a thin layer in accordance with the vacuum vapor deposition process or the coating process. It is preferable that the layer comprising the metal complex compound of the present invention is formed as a thin layer in accordance with the coating process since the production process can be simplified by using the coating process.

The metal complex compound of the present invention which is represented by general formula (1) can be synthesized via a plurality of routes as shown in the following. In the following, examples of the process for the synthesis will be described using Compound A, Compound B, Compound E and Compound F as the examples of the compound of the present invention.

(A) Compound A

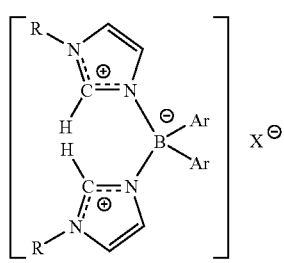

Compound A

In the above formula, R represents an alkyl group, Ar represents an aryl group, and X represents a halogen atom.

The above compound can be synthesized via two routes as follows. The metal atom is represented by M.

(A-1) A diaryl boron halide $Ar_2BX$ is obtained by the reaction of a metal aryl compound ArM with a boron trihalide $BX_3$ or an aryl boron dihalide $ArBX_2$, and Compound A can be obtained by bringing the obtained diaryl boron halide into reaction with a 1-alkyl-1,3-diazole.

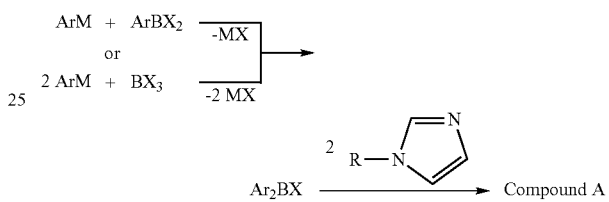

(A-2) A double ion pair shown in the following is obtained by the reaction of a 1-alkyl-1,3-diazole with an aryl boron dihalide $ArBX_2$, and Compound A can be obtained by bringing the obtained double ion pair into reaction with a metal aryl compound ArM.

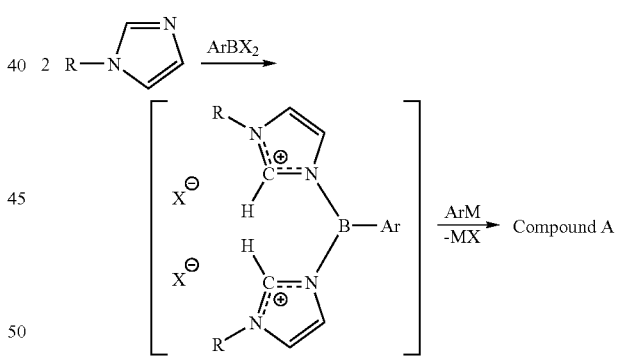

(B) Compound B

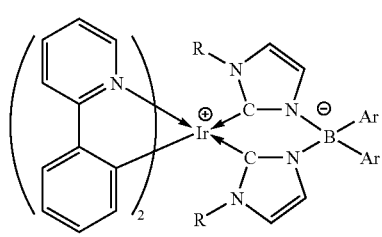

Compound B

This compound can be synthesized via two routes.

(B-1) Compound B can be obtained by treating a bridged dimer of a bis(2-phenylpyridine)iridium halide with a base (ZY), followed by bringing the obtained product into reaction with Compound A

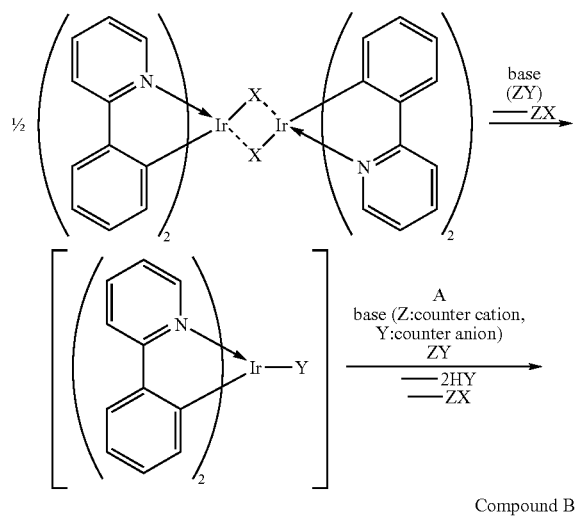

Compound B (B-2) Compound B can be obtained by bringing Compound C shown in the following, which is obtained by the reaction of Compound A with a base (ZY), into reaction with a bridged dimer of cyclooctadieneiridium chloride to obtain Compound D, followed by bringing the obtained Compound D into reaction with 2-phenylpyridine. Steps (a) and (b) may be conducted as a single step.

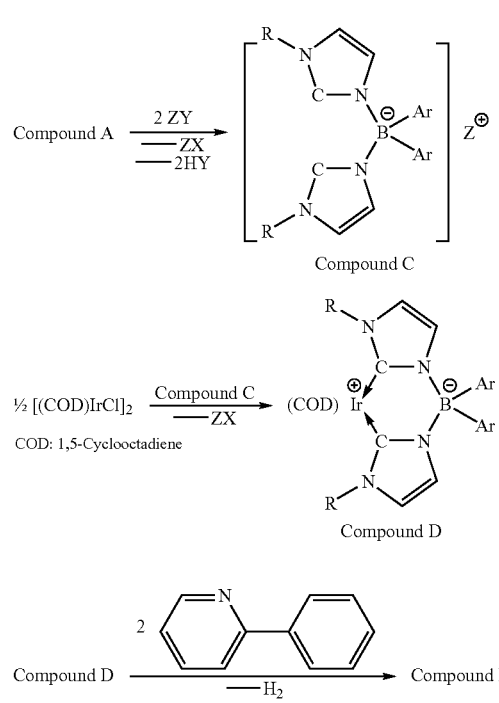

(C) Compound E

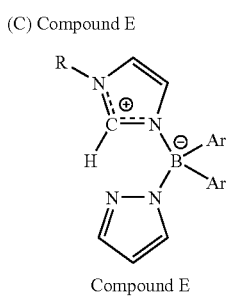

Compound E (C-1) As shown in the following, Compound E can be synthesized essentially via a route similar to the route described in (A-1).

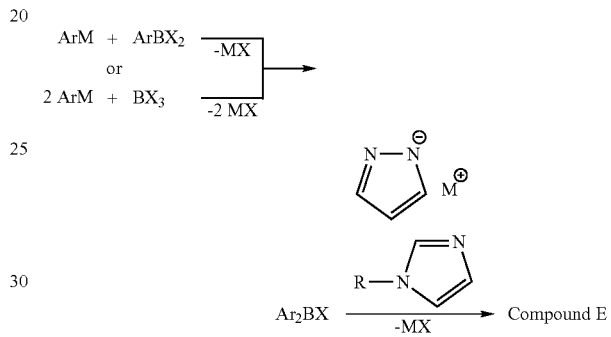

(C-2) As shown in the following, Compound E can be synthesized essentially via a route similar to the route described in (A-2).

(D) Compound F

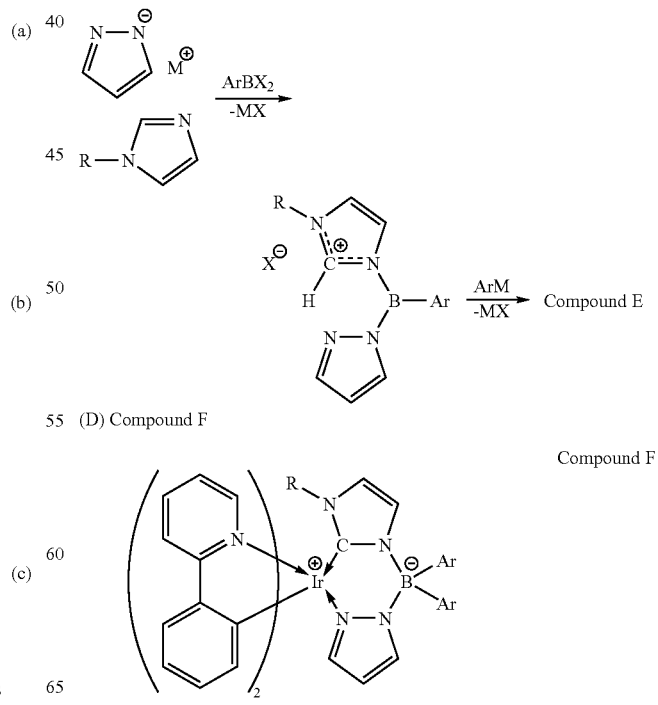

Compound F (D-1) Compound F can be synthesized by synthesizing Compound B in accordance with a process similar to the process described in (B-1), followed by bringing the obtained Compound B into the exchange reaction with Compound E obtained in (C).

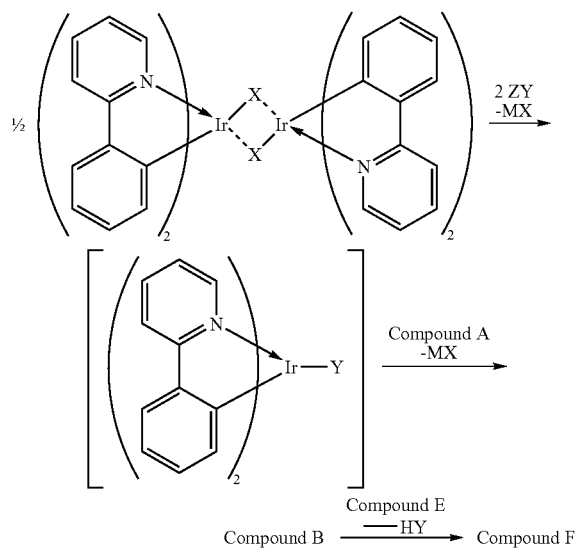

(D-2) Compound F can be obtained by synthesizing Compound D in accordance with a process similar to the process described in (B-2), followed by bringing the obtained Compound D into reaction with 2-phenylpyridine. Steps (a) and (b) may be conducted as a single step.

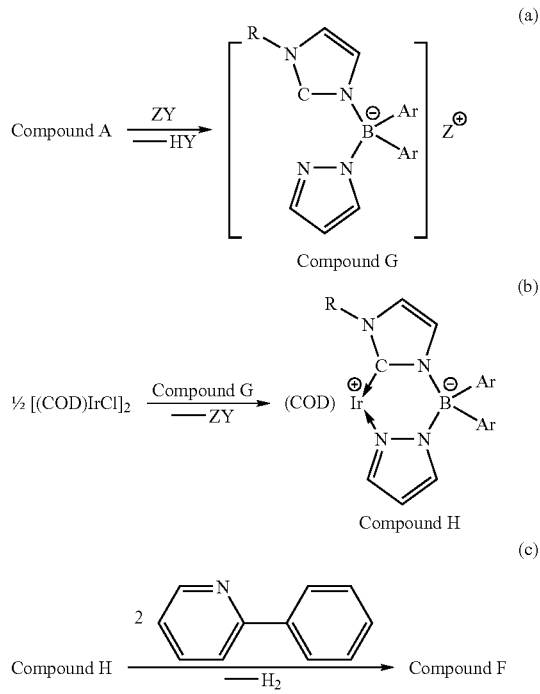

In the organic EL device of the present invention, when the organic thin film layer is a single layer, the organic thin film layer is the light emitting layer, and the light emitting layer comprises the metal complex compound of the present invention. When the organic thin film layer in the organic EL device comprises a plurality of layers, examples of the construction of the device include: (an anode/a hole injecting layer (a hole transporting layer)/a light emitting layer/a cathode), (an anode/a light emitting layer/an electron injecting layer (an electron transporting layer)/a cathode) and (an anode/a hole injecting layer (a hole transporting layer)/a light emitting layer/an electron injecting layer (an electron transporting layer)/a cathode).

The anode in the organic EL device of the present invention supplies holes to the hole injecting layer, the hole transporting layer and the light emitting layer, and it is effective that the anode has a work function of 4.5 eV or greater. As the material for the anode, metals, alloys, metal oxides, electrically conductive compounds and mixtures of these substances can be used. Examples of the material for the anode include electrically conductive metal oxides such as tin oxide, zinc oxide, indium oxide and indium tin oxide (ITO), metals such as gold, silver, chromium and nickel, mixtures and laminates of these electrically conductive metal oxides and metals, electrically conductive inorganic substances such as copper iodide and copper sulfide, electrically conductive organic substances such as polyaniline, polythiophene and polypyrrol and laminates of these substances with ITO. Conductive metal oxides are preferable, and ITO is more preferable from the standpoint of productivity, great electric conductivity and transparency. The thickness of the anode can be suitably selected in accordance with the material.

The cathode in the organic EL device of the present invention supplies electrons into the electron injecting layer, the electron transporting layer and the light emitting layer. As the material for the cathode, metals, alloys, metal halides, metal oxides, electrically conductive compounds and mixtures of these substances can be used. Examples of the material for the cathode include alkali metals (for example, Li, Na, K and the like), fluorides and oxides of alkali metals, alkaline earth metals (for example, Mg and Ca), fluorides and oxides of alkaline earth metals, gold, silver, lead, aluminum, sodium-potassium alloys, sodium-potassium mixed metals, lithium-aluminum alloys, lithium-aluminum mixed metals, magnesium-silver alloys, magnesium-silver mixed metals and rare earth metals such as indium and ytterbium. Among these materials, aluminum, lithium-aluminum alloys, lithium-aluminum mixed metals, magnesium-silver alloys and magnesium-silver mixed metals are preferable. The cathode may have a single layer structure comprising the above material or a laminate structure having a layer comprising the above material. For example, laminate structures having structures of aluminum/lithium fluoride and aluminum/lithium oxide are preferable. The thickness of the cathode can be suitably selected in accordance with the material.

As for the hole injecting layer and the hole transporting layer in the organic EL device of the present invention, it is sufficient that the layer has any of the function of injecting holes from the anode, the function of transporting holes and the function of forming a barrier to electrons injected from the cathode. Examples of the material for the hole injecting layer and the hole transporting layer include carbazole derivatives, triazole derivatives, oxazole derivatives, oxadiazole derivatives, imidazole derivatives, polyarylalkane derivatives, pyrazoline derivatives, pyrazolone derivatives, phenylenediamine derivatives, arylamine derivatives, chalcone derivatives substituted with amino group, styrylanthracene derivatives, fluorenone derivatives, hydrazone derivatives, stilbene derivatives, silazane derivatives, aromatic tertiary amine derivatives, styrylamine compounds, aromatic dimethylidine-based compounds, porphyrin-based compounds, polysilane-based compounds, poly(N-vinylcarbazole) derivatives, aniline-based copolymers, electrically conductive macromolecular oligomers such as thiophene oligomers and polythiophenes, organic silane derivatives and metal complex compounds of the present invention. The hole injecting layer and the hole transporting layer described above may have a structure having a single layer comprising at least one material selected from the above materials or a multi-layer structure having a plurality of layers comprising the same composition or different compositions.

As for the electron injecting layer and the electron transporting layer in the organic EL device of the present invention, it is sufficient that the layer has any of the function of injecting electrons from the cathode, the function of transporting electrons and the function of forming a barrier to holes injected from the anode. Examples of the material for the electron injecting layer and the electron transporting layer include triazole derivatives, oxazole derivatives, oxadiazole derivatives, imidazole derivatives, fluorenone derivatives, anthraquinodimethane derivatives, anthrone derivatives, diphenylquinone derivatives, thiopyran dioxide derivatives, carbodiimide derivatives, fluorenylidenemethane derivatives, distyrylpyrazine derivatives, tetracarboxylic acid anhydrides having an aromatic ring such as naphthalene ring and perylene ring, phthalocyanine derivatives, various metal complexes such as metal complexes of 8-quinolinol derivatives, metal complexes having phthalocyanine, benzoxazole or benzothiazole as the ligand, organic silane derivatives and the metal complex compounds of the present invention. The electron injecting layer and the electron transporting layer described above may have a structure having a single layer comprising at least one material selected from the above materials or a multi-layer structure having a plurality of layers comprising the same composition or different compositions.

Examples of the electron transporting material used for the electron injecting layer and the electron transporting layer include compounds shown in the following.

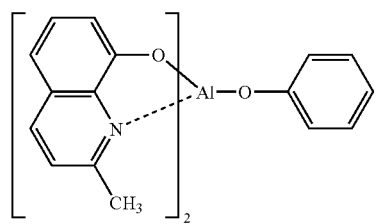
(A-1)

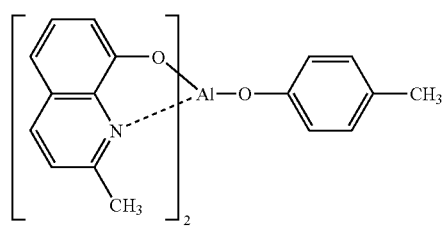
(A-2)

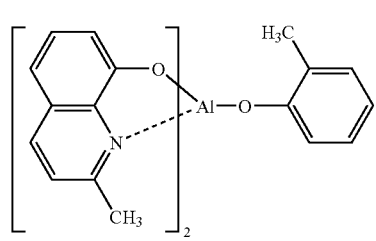
(A-3)

-continued

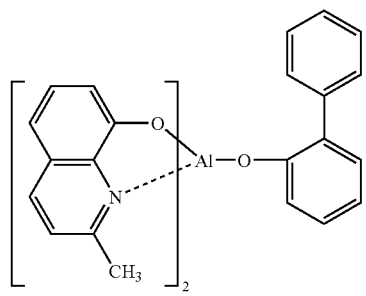
(A-4)

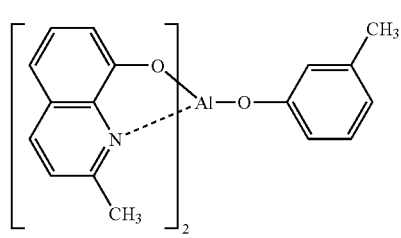
(A-5)

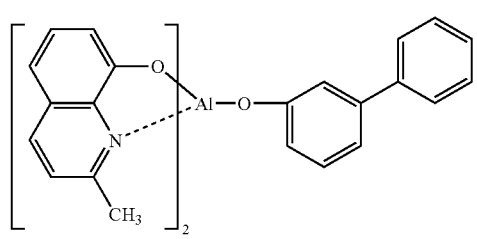
(A-6)

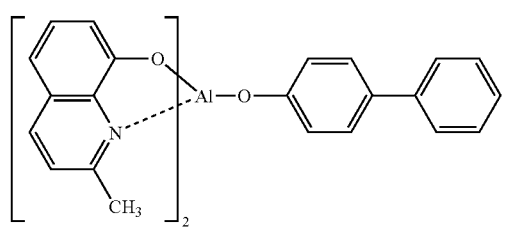
(A-7)

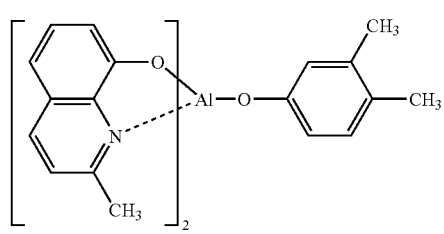
(A-8)

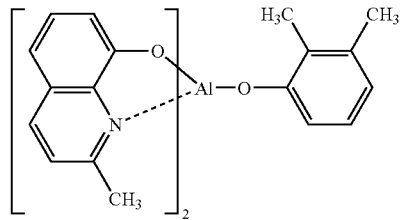
(A-9)

-continued
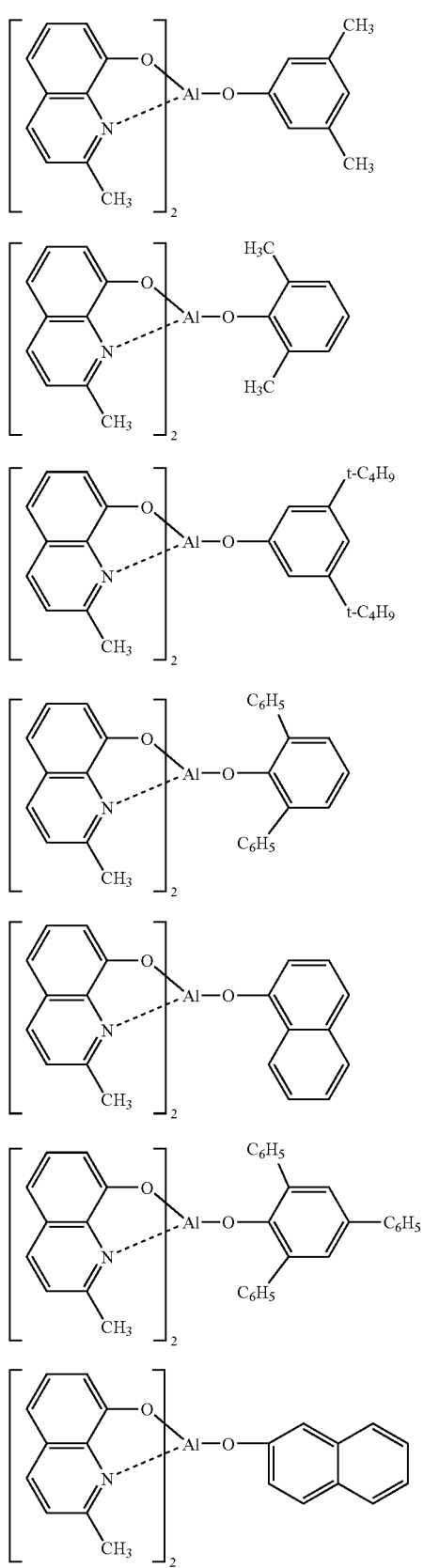
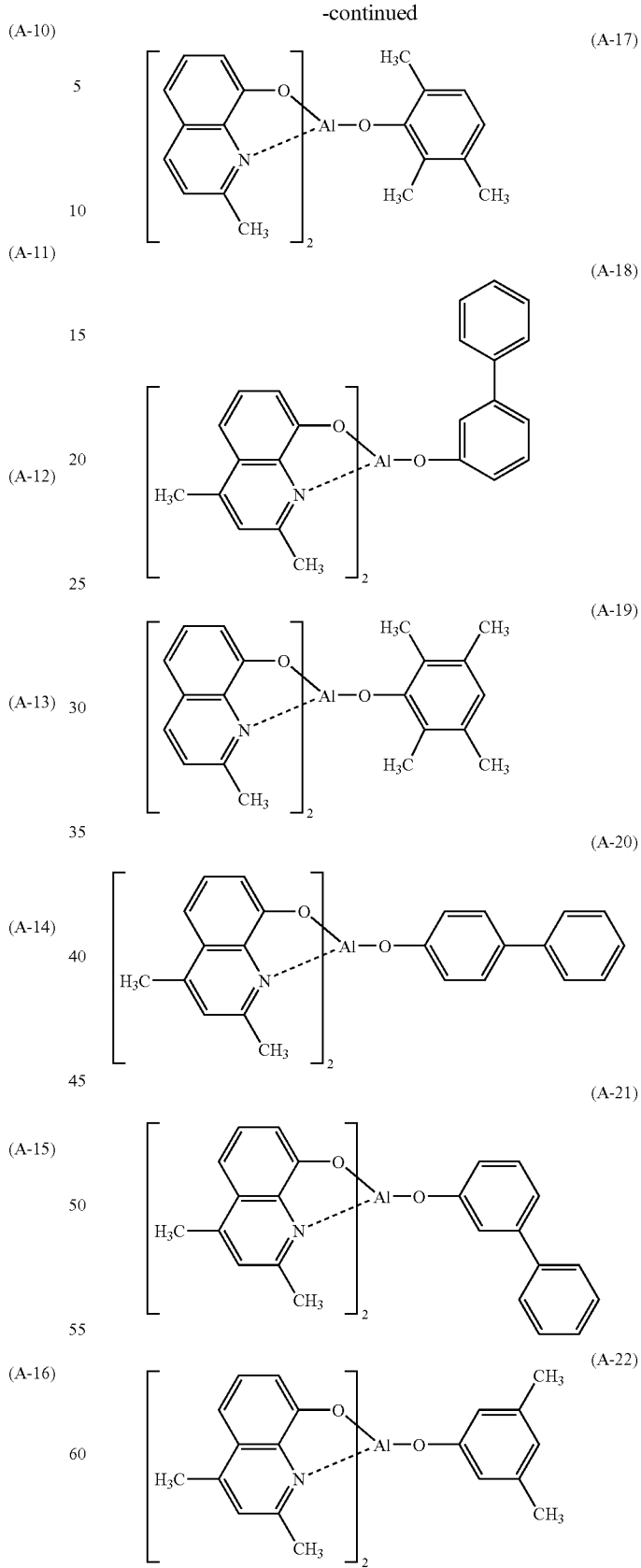

(A-23) 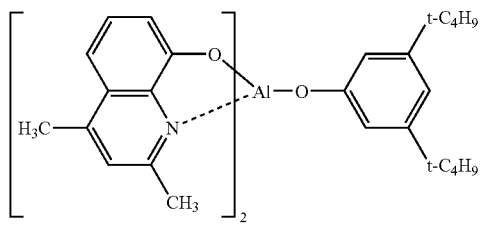
(A-24) 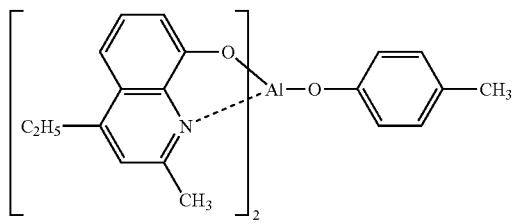
(A-25) 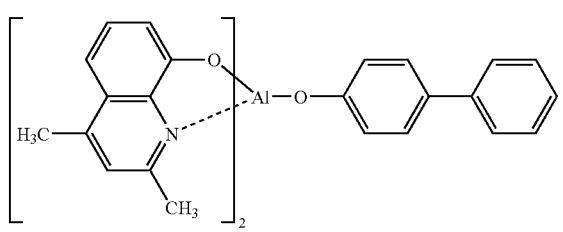
(A-26) 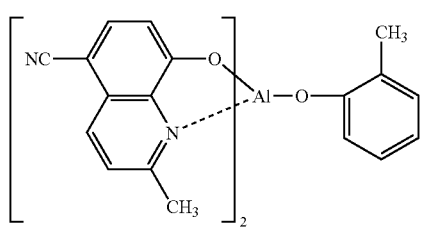
(A-27) 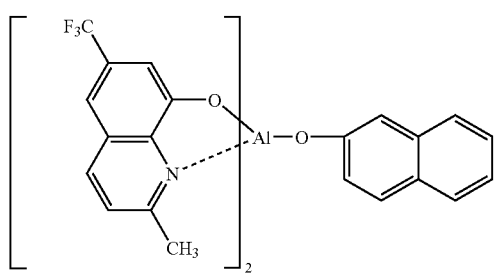
(A-28) 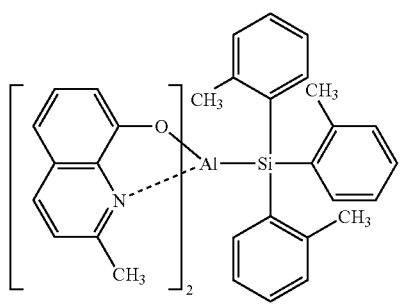
(A-29) 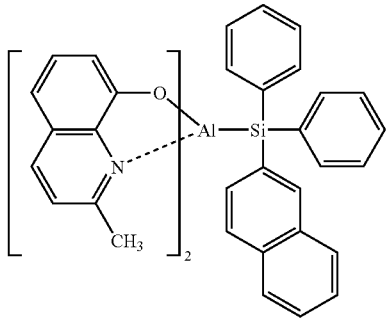
(A-30) 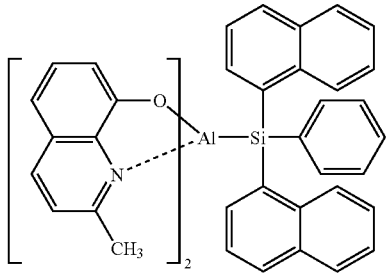
(A-31) 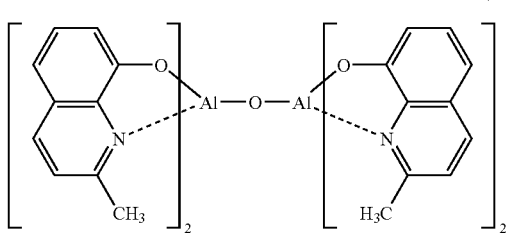
(A-32) 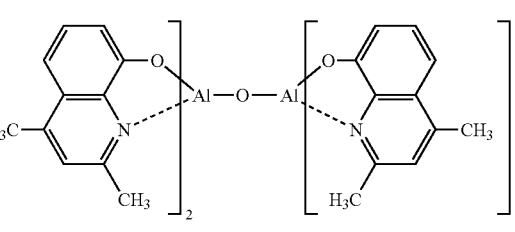
(A-33) 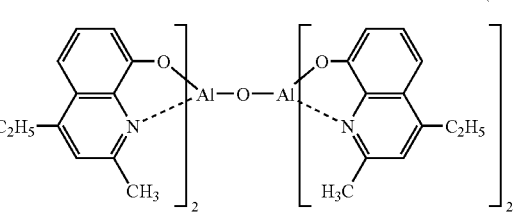
(A-34) 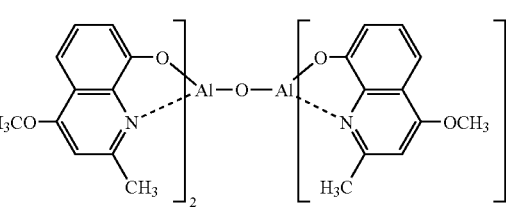

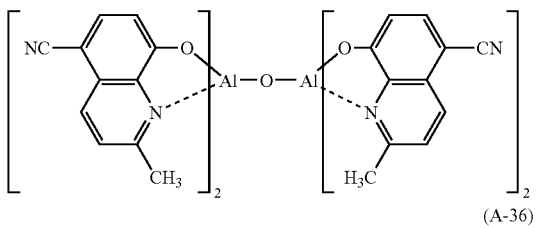

(A-35)

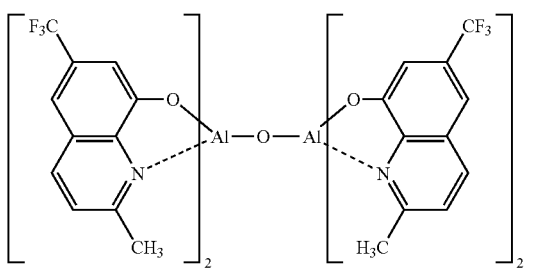

(A-36)

In the organic EL device of the present invention, it is preferable that the electron injecting layer and/or the electron transporting layer comprises a π-electron deficient heterocyclic derivative having nitrogen atom as the main component.

Preferable examples of the π-electron deficient heterocyclic derivative having nitrogen atom include derivatives having a five-membered ring having nitrogen atom selected from benzimidazole ring, benzotriazole ring, pyridinoimidazole ring, pyrimidinoimidazole ring, and pyridazinoimidazole ring and derivatives having a six-membered ring selected from pyridine ring, pyrimidine ring, pyrazine ring and triazine ring. As the five-membered ring having nitrogen atom, derivatives having structures represented by the following general formula B-I are preferable. As the six-membered ring having nitrogen atom, derivatives having structures represented by the following general formulae C-I, C-II, C-III, C-IV, C-V and C-VI are preferable. Derivatives having structures represented by general formulae C-I and C-II are more preferable.

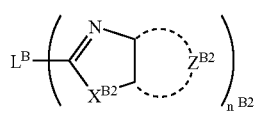

(B-I)

In general formula (B-I), $L^B$ represents a linking group having a valence of two or greater. The group is preferably a linking group formed with an atom or an ion such as carbon atom, silicon atom, nitrogen atom, boron atom, oxygen atom, sulfur atom, a metal atom and a metal ion; more preferably carbon atom, nitrogen atom, silicon atom, boron atom, oxygen atom, sulfur atom, an aromatic hydrocarbon rings or an aromatic heterocyclic rings; and most preferably carbon atom, silicon atom, aromatic hydrocarbon rings or an aromatic heterocyclic ring.

The group represented by $L^B$ may have substituents. As the substituent, alkyl groups, alkenyl groups, alkynyl groups, aromatic hydrocarbon groups, amino groups, alkoxyl groups, aryloxyl groups, acyl groups, alkoxycarbonyl groups, aryloxycarbonyl groups, acyloxyl groups, acylamino groups, alkoxycarbonylamino groups, aryloxycarbonylamino groups, sulfonylamino group, sulfamoyl group, carbamoyl group, alkylthio groups, arylthio groups, sulfonyl group, halogen atoms, cyano group and aromatic heterocyclic groups are preferable; alkyl groups, aryl groups, alkoxyl groups, aryloxyl groups, halogen atoms, cyano group and aromatic heterocyclic groups are more preferable; alkyl groups, aryl groups, alkoxyl groups, aryloxyl groups and aromatic heterocyclic groups are still more preferable; and alkyl groups, aryl groups, alkoxyl groups and aromatic heterocyclic groups are most preferable.

Examples of the bonding group represented by $L^B$ include groups shown in the following:

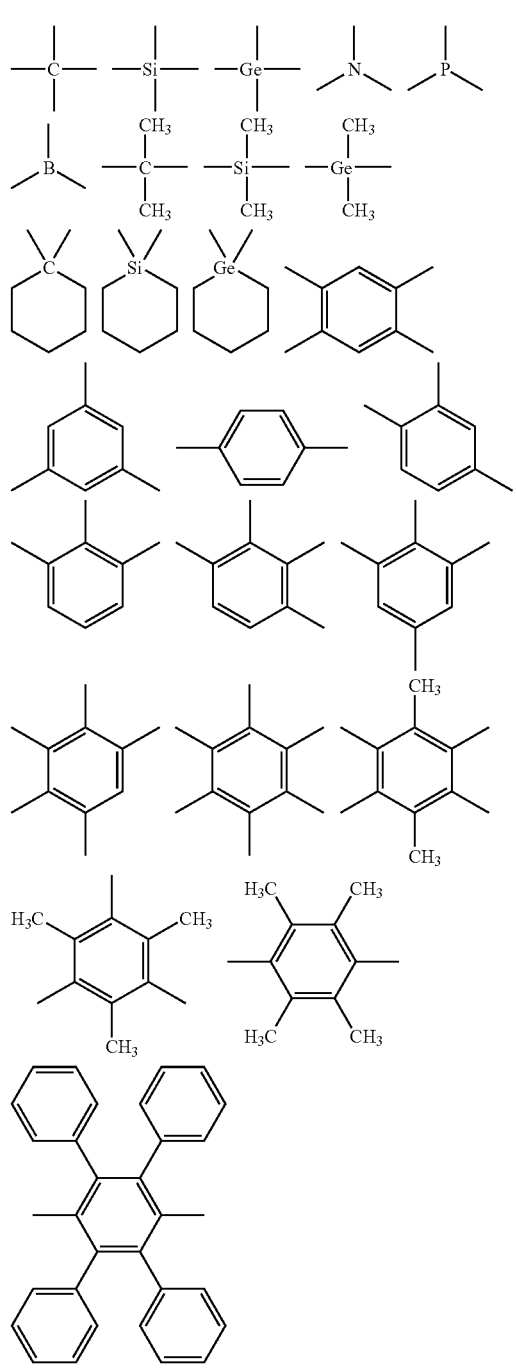

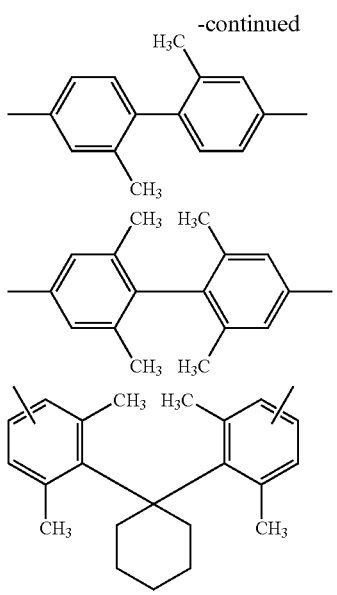

In formula (B-I), $X^{B2}$ represents —O—, —S— or a group represented by =N—$R^{B2}$. $R^{B2}$ represents hydrogen atom, an aliphatic hydrocarbon group, an aryl group or a heterocyclic group.

The aliphatic hydrocarbon group represented by $R^{B2}$ is a linear, branched or cyclic alkyl group (an alkyl group preferably having 1 to 20 carbon atoms, more preferably having 1 to 12 carbon atoms and most preferably having 1 to 8 carbon atoms, such as methyl group, ethyl group, isopropyl group, t-butyl group, n-octyl group, n-decyl group, n-hexadecyl group, cyclopropyl group, cyclopentyl group and cyclohexyl group), an alkenyl group (an alkenyl group preferably having 2 to 20 carbon atoms, more preferably having 2 to 12 carbon atoms and most preferably having 2 to 8 carbon atoms, such as vinyl group, allyl group, 2-butenyl group and 3-pentenyl group) or an alkynyl group (an alkynyl group preferably having 2 to 20 carbon atoms, more preferably having 2 to 12 carbon atoms and most preferably having 2 to 8 carbon atoms, such as propargyl group and 3-pentynyl group) and is preferably an alkyl group.

The aryl group represented by $R^{B2}$ is an aryl group having a single ring or a condensed ring preferably having 6 to 30 carbon atoms, more preferably having 6 to 20 carbon atoms and most preferably having 6 to 12 carbon atoms, such as phenyl group, 2-methylphenyl group, 3-methylphenyl group, 4-methylphenyl group, 2-methoxyphenyl group, 3-trifluoromethylphenyl group, pentafluorophenyl group, 1-naphthyl group and 2-naphthyl group.

The heterocyclic group represented by $R^{B2}$ is a heterocyclic group having a single ring or a condensed ring (a heterocyclic group preferably having 1 to 20 carbon atoms, more preferably having 1 to 12 carbon atoms and most preferably having 2 to 10 carbon atoms) and preferably an aromatic heterocyclic group having at least one of nitrogen atom, oxygen atom, sulfur atom and selenium atom. Specifically, the heterocyclic group is a group derived from pyrrolidine, piperidine, piperazine, morpholine thiophene, selenophene, furan, pyrrol, imidazole, pyrazole, pyridine, pyrazine, pyridazine, pyrimidine, triazole, triazine, indole, indazole, purine, thiazoline, thiazole, thiadiazole, oxazoline, oxazole, oxadiazole, quinoline, isoquinoline, phthalazine, naphthylidine, quinoxaline, quinazoline, cinnoline, pteridine, acridine, phenenthroline, phenazine, tetrazole, benzimidazole, benzoxazole, benzothiazole, benzotriazole, tetrazaindene, carbazole and azepine; preferably cyclic group derived from furan, thiophene, pyridine, pyrazine, pyrimidine, pyridazine, triazine, quinoline, phthalazine, naphthylidine, quinoxaline or quinazoline; more preferably a group derived from furan, thiophene, pyridine or quinoline; and most preferably a group derived from quinoline.

The aliphatic hydrocarbon group, the aryl group and the heterocyclic group represented by $R^{B2}$ may have substituents, and examples of the substituent include the substituents described above as the examples of the substituent to the group represented by $L^B$.

As the group represented by $R^{B2}$, alkyl groups, aryl groups and aromatic heterocyclic groups are preferable, aryl groups and aromatic heterocyclic groups are more preferable, and aryl groups are most preferable.

$X^{B2}$ preferably represents —O— or a group represented by =N—$R^{B2}$, more preferably a group represented by =N—$R^{B2}$, and most preferably a group represented by =N—$Ar^{B2}$ ($Ar^{B2}$, represents an aryl group (an aryl group preferably having 6 to 30 carbon atoms, more preferably having 6 to 20 carbon atoms and most preferably having 6 to 12 carbon atoms) or an aromatic heterocyclic group (an aromatic heterocyclic group preferably having 1 to 20 carbon atoms, more preferably having 1 to 12 carbon atoms and most preferably having 2 to 10 carbon atoms), and preferably an aryl group).

$Z^{B2}$ represents a group of atoms necessary for forming an aromatic ring. The aromatic ring formed with the group of atoms represented by $Z^{B2}$ may be any of an aromatic hydrocarbon ring and an aromatic heterocyclic ring. Examples of the aromatic ring include benzene ring, pyridine ring, pyrazine ring, pyrimidine ring, pyridazine ring, triazine ring, pyrrol ring, furan ring, thiophene ring, selenophene ring, tellurophene ring, imidazole ring, thiazole ring, selenazole ring, tellurazole ring, thiadiazole ring, oxadiazole ring and pyrazole ring. Among these rings, benzene ring, pyridine ring, pyrazine ring, pyrimidine ring and pyridazine ring are preferable, benzene ring, pyridine ring and pyrazine ring are more preferable, benzene ring and pyridine ring are still more preferable, and pyridine ring is most preferable. The aromatic ring formed with the group of atoms represented by $Z^{B2}$ may form a condensed ring in combination with other rings and may have substituents. As the substituent, alkyl groups, alkenyl groups, alkynyl groups, aryl groups, amino groups, alkoxyl groups, aryloxyl groups, acyl groups, alkoxycarbonyl groups, aryloxycarbonyl groups, acyloxyl groups, acylamino groups, alkoxycarbonylamino groups, aryloxycarbonylamino groups, sulfonylamino group, sulfamoyl group, carbamoyl group, alkylthio groups, arylthio groups, sulfonyl group, halogen atoms, cyano group and heterocyclic groups are preferable, alkyl groups, aryl groups, alkoxyl groups, aryloxyl groups, halogen atoms, cyano group and heterocyclic groups are more preferable, alkyl groups, aryl groups, alkoxyl groups, aryloxyl groups and aromatic heterocyclic groups are still more preferable, and alkyl groups, aryl groups, alkoxyl groups and aromatic heterocyclic groups are most preferable.

$n^{B2}$ represents an integer of 1 to 4 and preferably 2 or 3.

Among the compounds represented by the above general formula (B-I), compounds represented by the following general formula (B-II) are preferable.

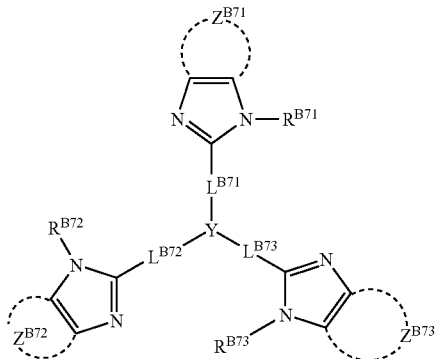
(B-II)

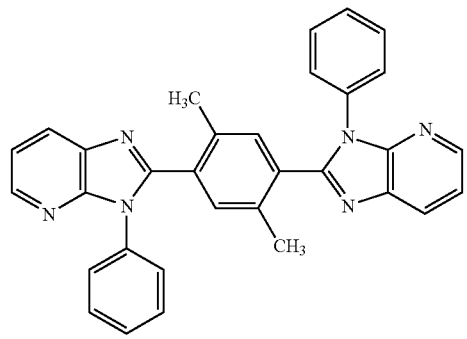
(B-2)

In general formula (B-II), $R^{B71}$, $R^{B72}$ and $R^{B73}$ are each as defined for $R^{B2}$ in $X^{B2}$ of general formula (B-I), and the preferable groups are the same as those for $R^{B72}$.

$Z^{B71}$, $Z^{B72}$ and $Z^{B73}$ are each as defined for $Z^{B72}$ in general formula (B-I), and the preferable groups are the same as those for $Z^{B72}$.

$L^{B71}$, $L^{B72}$ and $L^{B73}$ each represent a bonding group. Examples of the group include divalent groups derived from the groups described as the examples of the group represented by $L^B$ in general formula (B-I). The bonding group is preferably the single bond, a divalent aromatic hydrocarbon cyclic group, a divalent aromatic heterocyclic group or a bonding group obtained as a combination of these groups, and more preferably the single bond. The groups represented by $L^{B71}$, $L^{B72}$ and $L^{B73}$ may have substituents. Examples of the substituent include the substituents described as the examples of the substituent for the groups represented by $L^B$ in general formula (B-I).

Y represents nitrogen atom, 1,3,5-benzenetriyl group or 2,4,6-triazinetriyl group. 1,3,5-Benzenetriyl group may have substituents at the 2-, 4- and 6-positions. Examples of the substituent include alkyl groups, aromatic hydrocarbon cyclic groups and halogen atoms.

Examples of the five-membered cyclic derivative having nitrogen atom which is represented by general formula (B-I) or (B-II) are shown in the following. However, the five-membered cyclic derivative having nitrogen atom is not limited to the compounds shown as the examples.

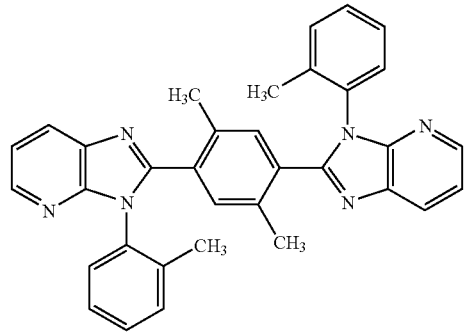
(B-3)

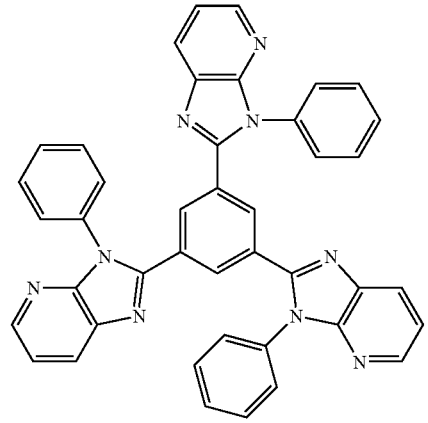
(B-4)

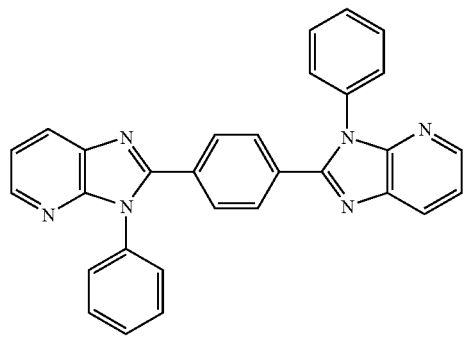
(B-1)

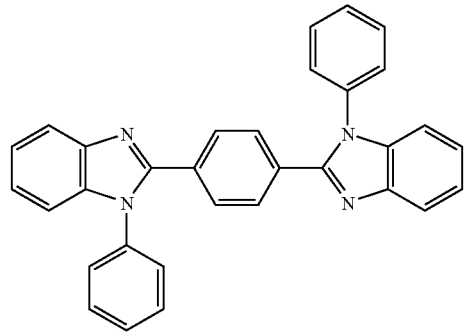
(B-5)

-continued
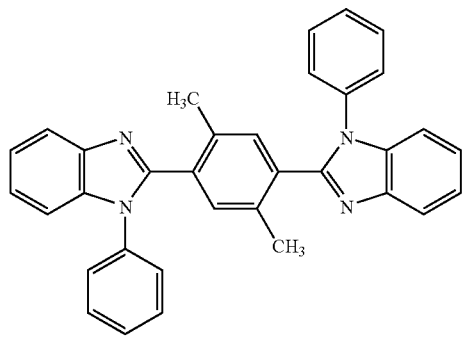
(B-6)
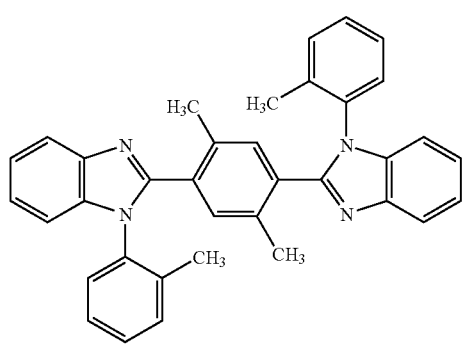
(B-7)
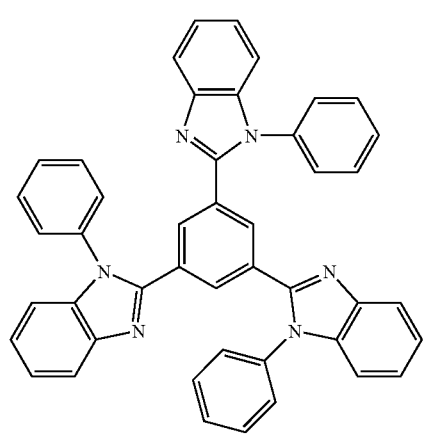
(B-8)
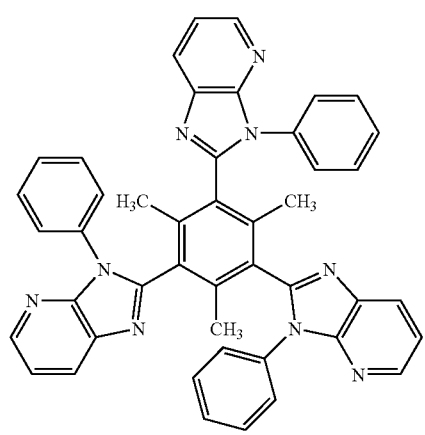
(B-9)
-continued
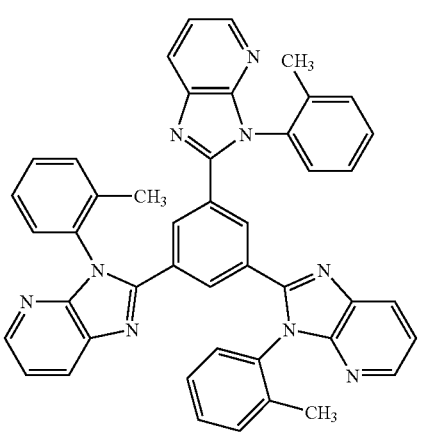
(B-10)
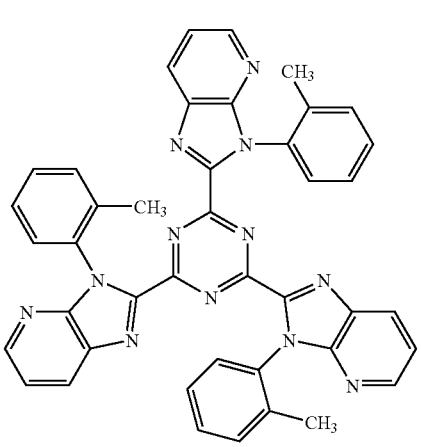
(B-11)
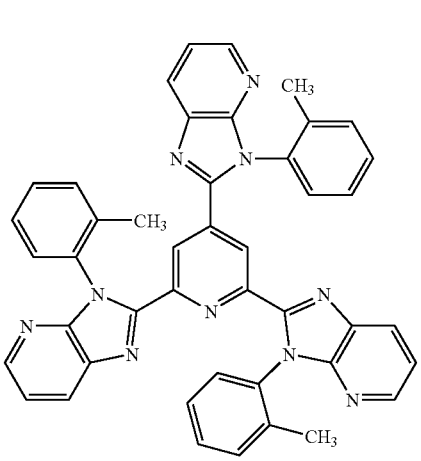
(B-12)

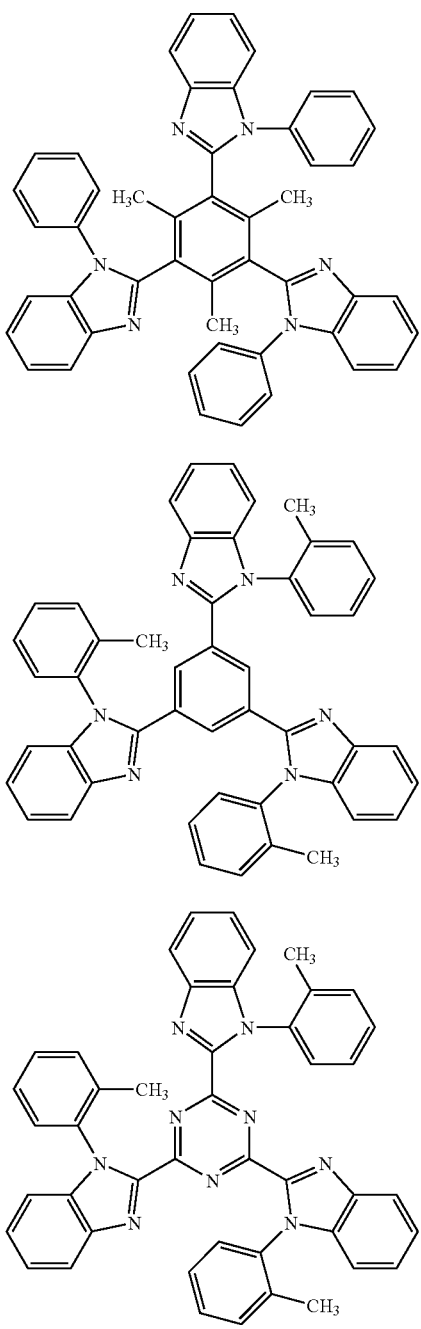

(B-13)

(B-14)

(B-15)

(B-16)

$$(Cz\text{—})_n A \quad \text{(C-I)}$$

$$Cz(\text{—}A)_m \quad \text{(C-II)}$$

[In the above formulae, Cz represents a substituted or unsubstituted carbazolyl group, arylcarbazolyl group or carbazolyalkylene group, A represents a group formed with a portion represented by the following general formula (A), and n and m each represent an integer of 1 to 3.

$$(M)_p\text{-}(L)_q\text{-}(M')_r \quad \text{(A)}$$

(M and M' each independently represent a heteroaromatic ring having 2 to 40 carbon atoms forming the ring and nitrogen atom, and the ring may have substituents or no substituents. The groups represented by M and M' may be the same with or different from each other. L represents the single bond, an arylene group having 6 to 30 carbon atoms, a cycloalkylene group having 5 to 30 carbon atoms or a heteroaromatic ring having 2 to 30 carbon atoms, and the ring may have substituents or no substituents bonded to the ring. p represents an integer of 0 to 2, r represents an integer of 0 to 2, and p+r represents an integer 1 or greater.)]

The bonding mode of general formulae (C-I) and (C-II) can be expressed more specifically as shown in the following table in accordance with the values of the parameters n and m.

| n = m = 1 | n = 2 | n = 3 | m = 2 | m = 3 |
|---|---|---|---|---|
| Cz—A | Cz—A—Cz | Cz—A(—Cz)—Cz | A—Cz—A | A—Cz(—A)—A |

The bonding mode of the group represented by general formula (A) can be expressed more specifically as shown by (1) to (16) in the following table in accordance with the values of the parameters p, q and r.

| No | p | q | r | Bonding mode |
|---|---|---|---|---|
| (1) | 0 | 1 | 1 | L—M' |
| (2) | 0 | 1 | 2 | L—M'—M', M'—L—M' |
| (3) | 0 | 2 | 1 | L—L—M', L—M'—L |

-continued

| No | p | q | r | Bonding mode |
|---|---|---|---|---|
| (4) | 0 | 2 | 2 | L—L—M'—M', M'—L—L—M',<br>L—M'—M'—L,  M'—L—M',  L—M'—L<br>  \|       \|              \|              \|<br>  L       L              L              M' |
| (5) | 1 | 1 | 0 | the same as (1) (replacing M' with M) |
| (6) | 1 | 1 | 1 | M—L—M' |
| (7) | 1 | 1 | 2 | M—L—M'—M',<br>M—L—M'<br>      \|<br>      M' |
| (8) | 1 | 2 | 0 | the same as (3) (replacing M' with M) |
| (9) | 1 | 2 | 1 | M—L—L—M', L—M—L—M', M—L—M'—L |
| (10) | 1 | 2 | 2 | M—L—L—M'—M', M'—L—M—L—M',<br>M'—M'—L—M—L,<br>M—L—L,  M—L—L—M',  L—L—M'—M',<br>  \|  \|           \|                    \|<br>  M' M'          M'                   M<br>                          M'<br>                          \|<br>L—M—L—M',  M—L—L<br>      \|              \|<br>      M'            M' |
| (11) | 2 | 1 | 0 | the same as (2) (replacing M' with M) |
| (12) | 2 | 1 | 1 | the same as (7) (replacing M' with M) |
| (13) | 2 | 1 | 2 | M—M—L—M'—M',<br>        M'<br>         \|<br>M—L—M,  M—L—M'—M'<br>    \|             \|<br>    M'            M |
| (14) | 2 | 2 | 0 | the same as (4) (replacing M' with M) |
| (15) | 2 | 2 | 1 | the same as (10) (replacing M' with M) |
| (16) | 2 | 2 | 2 | M—M—L—L—M'—M',<br>                                                              M<br>                                                              \|<br>M—M—L—M'—M', M—L—L—M'—M',  M—L—L,<br>        \|                   \|                      M'/  \M'<br>        L                   M<br>                          M<br>                          \|<br>M—M—L—L—M',  L—L—M'—M',  M—L—L—M<br>        \|              \|                 \|   \|<br>        M'             M                M'  M' |

When the group represented by Cz is bonded to the group represented by A in the above general formulae (C-I) and (V-II), the group represented by Cz may be bonded to any position of the group or the ring represented by M, L and M' in general formula (A). For example, in the case of m=n=1 (Cz-A) and p=q=r=1 ((6) in the table), the group represented by A becomes a group represented by M-L-M', and the structure is expressed by the three bonding modes of Cz-M-L-M', M-L(-Cz)-M' and M-L-M'-Cz. Similarly, for example, in the case of n=2 (Cz-A-Cz) in general formula (C-I) and p=q=1 and r=2 ((7) in the table), the group represented by A becomes a group represented by M-L-M'-M' or M-L(-M')-M', and the structure is expressed by the following bonding modes:

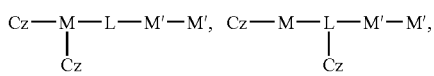

-continued

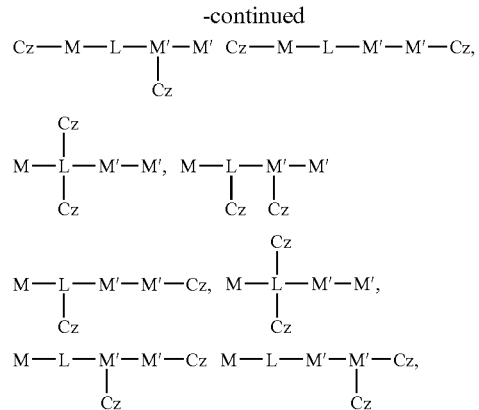

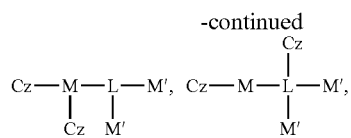
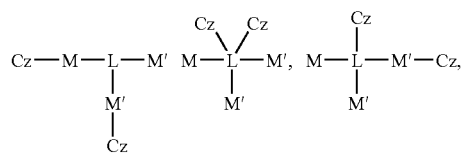
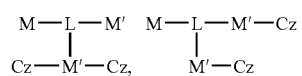
Examples of the six-membered cyclic derivative having nitrogen atom which is represented by general formula (C-I) or (C-II) are shown in the following. However, the derivative is not limited to the compounds shown as the examples.
(C-1)
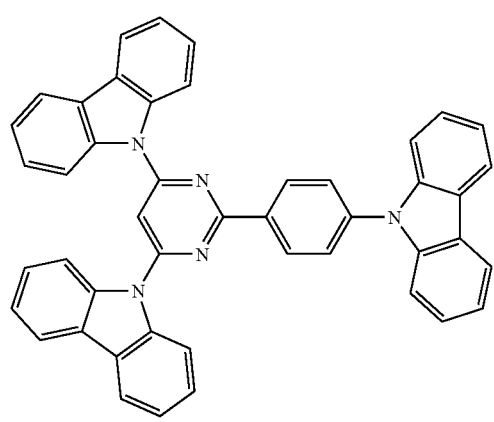
(C-2)
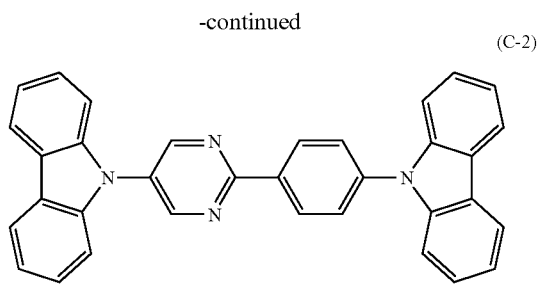
(C-3)
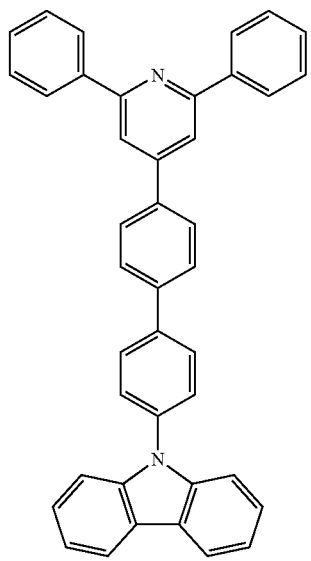
(C-4)
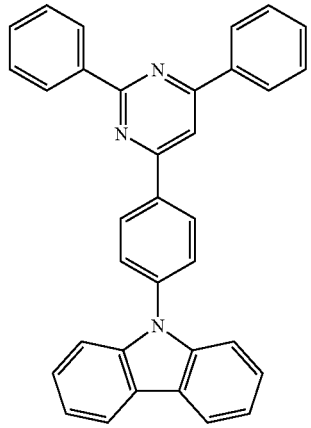

-continued
(C-5)
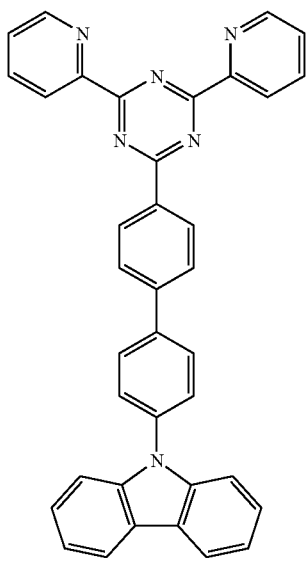
(C-7)
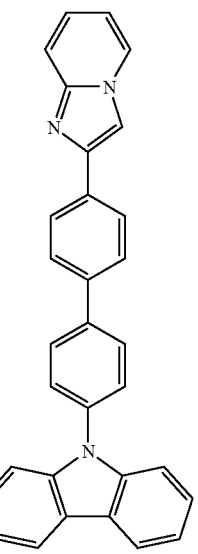
(C-6)
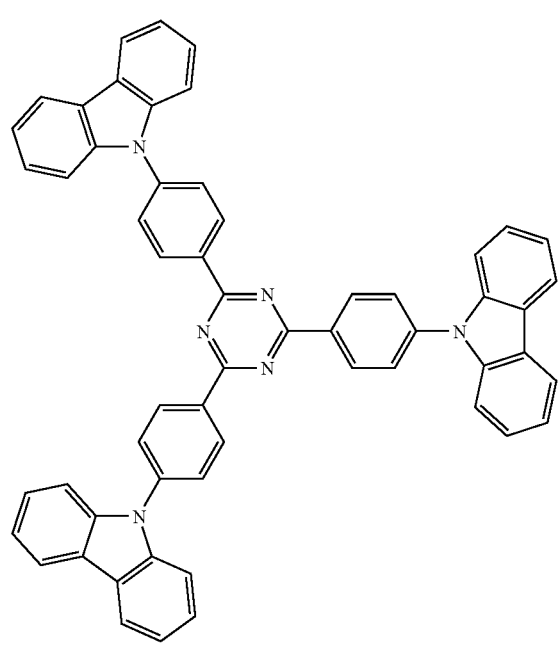
(C-8)
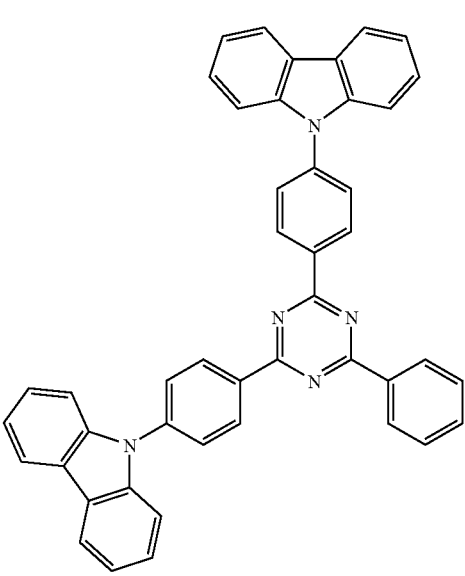

-continued
(C-9)
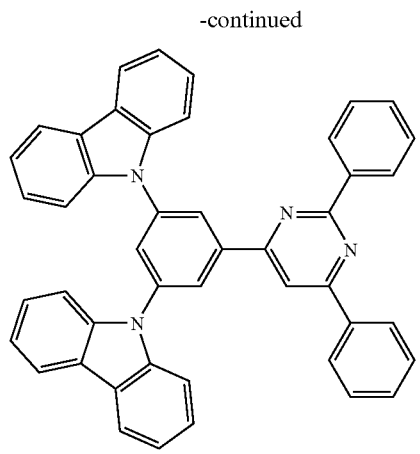
(C-12)
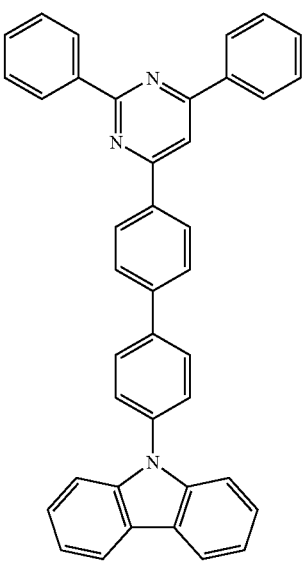
(C-10)
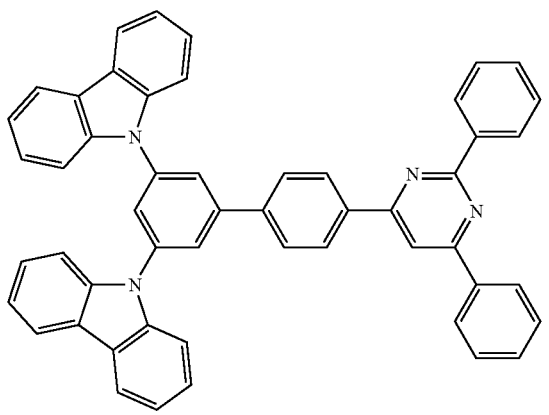
(C-11)
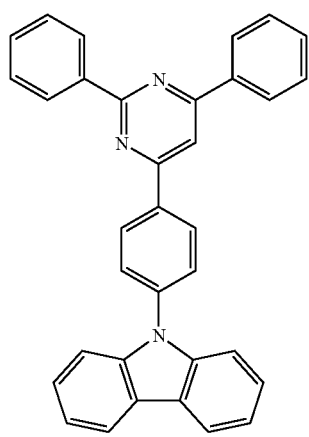
(C-13)
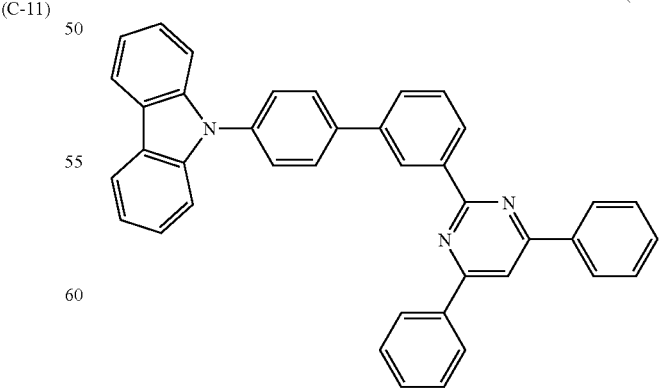

(C-14)

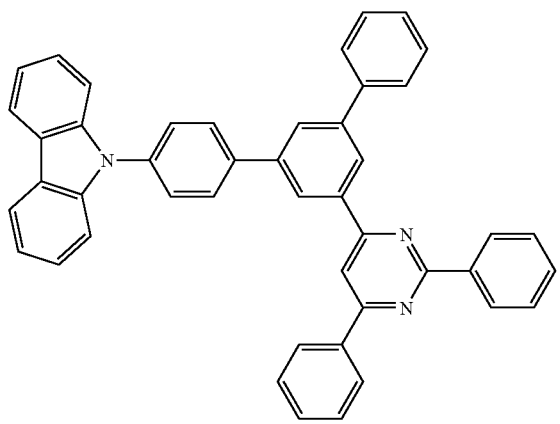

(C-15)

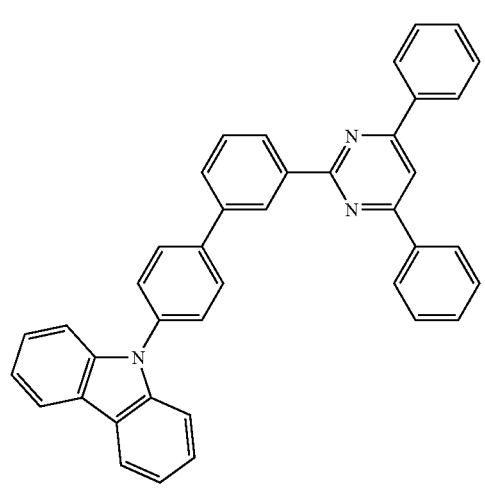

(C-III)

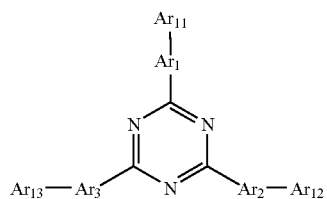

(In the above formula, $Ar_{11}$ to $Ar_{13}$ each represent the same group as the group represented by $R^{B2}$ in general formula (B-1), and examples of the group include the groups described as the examples of the group represented by $R^{B2}$. $Ar_1$ to $Ar_3$ each represent a divalent group derived from the group represented by $R^{B2}$ in general formula (B-1), and example of the group include divalent groups derived from the groups described as the examples of the group represented by $R^{B2}$.

Examples of the derivative represented by general formula (C-III) are shown in the following. However, the derivative is not limited to the compounds shown as the examples.

(C-IV)

$$\begin{array}{c} R_{60} \\ R_{61} \overset{|}{\underset{R_{62}}{\bigvee}} N \\ \phantom{R_{62}} \overset{N}{\underset{N}{\bigvee}} R_{59} \end{array}$$

(In the above formula, $R_{59}$ to $R_{62}$ each represent the same group as the group represented by $R^{B2}$ in general formula (B-1), and examples of the group include the groups described as the examples of the group represented by $R^{B2}$.)

Examples of the derivative represented by general formula (C-IV) are shown in the following. However, the derivative is not limited to the compounds shown as the examples.

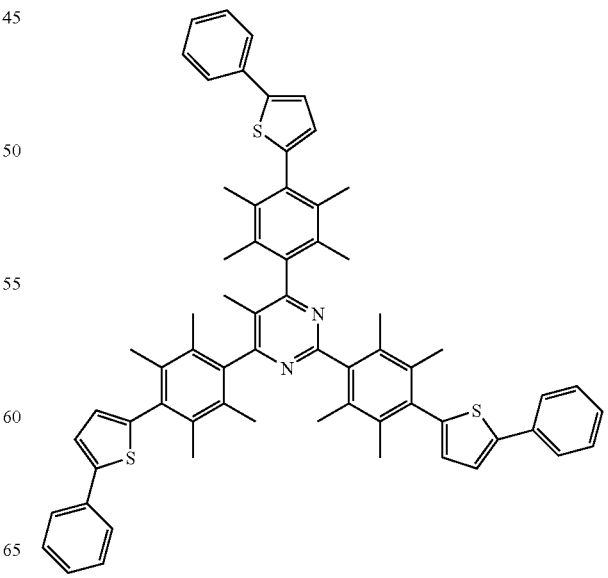

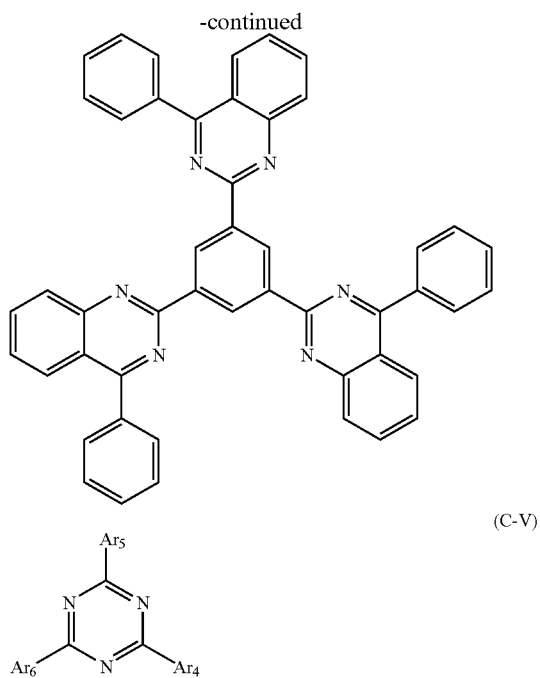

(C-V)

(In the above formula, $Ar_4$ to $Ar_6$ each represent the same group as the group represented by $R^{B2}$ in general formula (B-1), and examples of the group include the groups described as the examples of the group represented by $R^{B2}$.)

Examples of the derivative represented by general formula (C-V) are shown in the following. However, the derivative is not limited to the compounds shown as the examples.

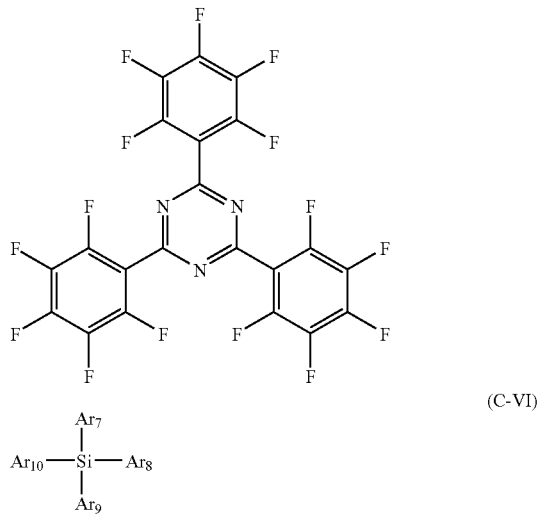

(C-VI)

(In the above formula, $Ar_7$ to $Ar_{10}$ each represent the same group as the group represented by $R^{B2}$ in general formula (B-1), and examples of the group include the groups described as the examples of the group represented by $R^{B2}$.)

An examples of the derivative represented by general formula (C-VI) is shown in the following. However, the derivative is not limited to the compounds shown as the examples.

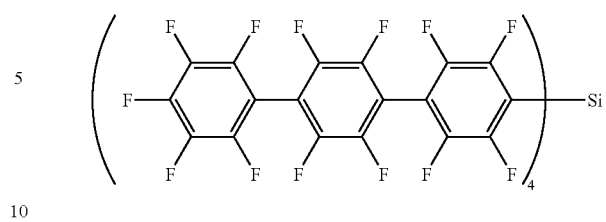

In the organic EL device of the present invention, it is preferable that an insulating material or a semiconducting inorganic compound is used as the substance constituting the electron injecting and transporting layer. When the electron injecting and transporting layer is constituted with an insulating material or a semiconductor, leak of the electric current can be effectively prevented, and the electron injecting property can be improved. As the insulating material, at least one metal compound selected from the group consisting of chalcogenides of alkali metals, chalcogenides of alkaline earth metals, halides of alkali metals and halides of alkaline earth metals is preferable. It is preferable that the electron injecting layer or transporting layer is constituted with the above metal compound since the electron injecting property can be further improved.

Preferable examples of the chalcogenide of an alkali metal include $Li_2O$, $Na_2S$ and $Na_2Se$. Preferable examples of the chalcogenide of an alkaline earth metal include CaO, BaO, SrO, BeO, BaS and CaSe. Preferable examples of the halide of an alkali metal include LiF, NaF, KF, LiCl, KCl and NaCl. Preferable examples of the halide of an alkaline earth metal include fluoride such as $CaF_2$, $BaF_2$, $SrF_2$, $MgF_2$ and $BeF_2$ and halides other than the fluorides.

Examples of the semiconductor constituting the electron transporting layer include oxides, nitrides and oxide nitrides comprising at least one element selected from Ba, Ca, Sr, Yb, Al, Ga, In, Li, Na, Cd, Mg, Si, Ta, Sb and Zn used singly or in combination of two or more. It is preferable that the inorganic compound constituting the electron transporting layer forms a crystallite or amorphous insulating thin film. When the electron transporting layer is constituted with the insulating thin film described above, a more uniform thin film can be formed, and defects of pixels such as dark spots can be decreased. Examples of the inorganic compound include chalcogenides of alkali metals, chalcogenides of alkaline earth metals, halides of alkali metals and halides of alkaline earth metals which are described above.

In the organic EL device of the present invention, the electron injecting layer and/or the electron transporting layer may comprise a reducing dopant having a work function of 2.9 eV or smaller. In the present invention, the reducing dopant is a compound which increases the efficiency of injecting electrons.

In the present invention, it is preferable that the reducing dopant is added into an interfacial region between the cathode and the organic thin film layer. At least a portion of the organic layer contained in the interfacial region is reduced to form anions. At least one substance selected from the group consisting of alkaline metals, oxides of alkaline earth metals, alkaline earth metals, rare earth metals, oxides of alkaline metals, halides of alkaline metals, oxides of alkaline earth metals, halides of alkaline earth metals, oxides of rare earth metals, halides of rare earth metals, complex compounds of alkali metals, complex compounds of alkaline earth metals and complex compounds of rare earth metals is preferable as the reducing dopant. More specifically, at least one alkali metal selected from the group consisting of Na (the work function: 2.36 eV), K (the work function: 2.28 eV), Rb (the work function: 2.16 eV) and Cs (the work function: 1.95 eV) and at least one alkaline earth metal selected from the group consisting of Ca (the work function: 2.9 eV), Sr (the work function: 2.0 to 2.5 eV) and Ba (the work function: 2.52 eV), are preferable. Substances having a work function of 2.9 eV or smaller are preferable. Among the above substances, at least one alkali metal selected from the group consisting of K, Rb and Cs is more preferable, Rb and Cs are still more preferable, and Cs is most preferable as the reducing dopant. These alkali metals have great reducing ability, and the luminance of the emitted light and the life of the organic EL device can be increased by addition of a relatively small amount into the electron injecting zone.

As the oxide of an alkaline earth metal, for example, BaO, SrO, CaO and $Ba_xSr_{1-x}O$ (O<x<1) and $Ba_xCa_{1-x}$ (O<x<1) which are obtained by mixing the oxides are preferable. Examples of the oxide of an alkaline metal and the fluoride of an alkaline metal include LiF, $Li_2O$ and NaF. The alkaline metal complex compound, the alkaline earth metal complex compound and the rare earth metal complex compound are not particularly limited as long as the compound comprises at least one of the alkaline metal ions, the alkaline earth metal ions and the rare earth metal ions. Examples of the ligand include quinolinol, benzoquinolinol, acrydinol, phenanthridinol, hydroxyphenyloxazole, hydroxyphenylthiazole, hydroxydiaryloxadiazoles, hydroxydiarylthiadiazoles, hydroxyphenyl-pyridine, hydroxyphenylbenzimidazole, hydroxybenzotriazole, bipyridyl, phenanthroline, phthalocyanine, porphyrin, cyclopentadiene, β-diketones, azomethines and derivatives of these ligands. However the ligand is not limited to those described above.

As for the form of the reducing dopant, it is preferable that the reducing dopant is formed as a layer or islands. When the reducing dopant is used by forming a layer, it is preferable that the thickness of the layer is 0.05 to 8 nm.

As the process for forming the electron injecting and transporting layer comprising the reducing dopant, it is preferable that a light emitting material for forming the interfacial region or an organic substance as the electron injecting material is simultaneously vapor deposited with the reducing dopant while the reducing dopant is vapor deposited in accordance with the vapor deposition process using the resistance heating so that the reducing dopant is dispersed in the organic substance. The concentration of the dispersion is 100:1 to 1:100 and preferably 5:1 to 1:5 as the ratio of the amounts by mole. When a layer of the reducing dopant is formed, a layer of a light emitting material or an electron injecting material which is the organic layer at the interface is formed. Then, the reducing dopant alone is vapor deposited in accordance with the vapor deposition process using the resistance heating, and a layer preferably having a thickness of 0.5 to 15 nm is formed. When islands of the reducing dopant is formed, a layer of a light emitting material or an electron injecting material which is the organic layer at the interface is formed. Then, the reducing dopant alone is vapor deposited in accordance with the vapor deposition process using the resistance heating, and islands preferably having a thickness of 0.05 to 1 nm are formed.

The light emitting layer in the organic EL device of the present invention has the function of injecting holes from the anode or the hole injecting layer and injecting electrons from the cathode or the electron injecting layer when an electric field is applied, the function of transferring the injected charges (electrons and holes) by the force of the electric field, and the function of providing the field for recombination of electrons and holes, leading the recombination to the emission of light. It is preferable that the light emitting layer in the organic EL device of the present invention comprises at least the metal complex compound of the present invention and may comprise a host material for using the metal complex compound as the guest material. Examples of the host material include materials having the skeleton structures of carbazole, a diarylamine, pyridine, pyrazine, triazine and an arylsilane. It is preferable that T1 (the energy level of the lowest excited state of the triplet) is greater than T1 of the guest material. The host material may be a low molecular weight compound or a macromolecular compound. A light emitting layer in which the host material is doped with the light emitting material can be formed by the simultaneous vapor deposition of the host material and the light emitting material such as the metal complex compound described above.

The process for forming the layers described above in the organic EL device of the preset invention is not particularly limited. Various processes such as the vacuum vapor deposition process, the LB process, the vapor deposition process using the resistance heating, the electron beam process, the sputtering process, the molecular accumulation process, the coating process (such as the spin coating process, the casting process and the dip coating process), the ink jet process and the printing process can be used. In the present invention, the coating process is preferable.

The organic thin film layer comprising the metal complex compound of the present invention can be formed in accordance with a conventional process such as the vacuum vapor deposition process, the molecular beam epitaxy process (the MBE process), or a coating process using a solution prepared by dissolving the metal complex compound into a solvent. Examples of the coating process include the dipping process, the spin coating process, the casting process, the bar coating process and the roll coating process.

In the above coating process, the metal complex compound of the present invention is dissolved into a solvent to prepare a coating fluid, and the layer can be formed by applying the coating fluid to a desired layer (or an electrode) and drying the formed coating layer. The coating fluid may comprises a resin. The resin may be used in the condition dissolved in the solvent or dispersed in the solvent. As the resin, macromolecules based on non-conjugated compounds (for example, polyvinyl carbazole) and macromolecules based on conjugated compounds (for example, polyolefin-based macromolecules) can be used. Examples of the resin include polyvinyl chloride, polycarbonates, polystyrene, polymethyl methacrylate, polybutyl methacrylate, polyesters, polysulfone, polyphenylene oxide, polybutadiene, poly(N-vinylcarbazole), hydrocarbon resins, ketone resins, phenoxy resins, polyamides, ethylcellulose, vinyl acetate resins, ABS resins, polyurethanes, melamine resins, unsaturated polyester resins, alkyd resins, epoxy resins and silicone resins.

The thickness of each organic layer in the organic EL device of the present invention is not particularly limited. In general, an excessively small thickness tends to form defects such as pin holes, and an excessively great thickness requires application of a high voltage to decrease the efficiency. In general, it is preferable that the thickness is in the range of several nm to 1 μm.

EXAMPLES

As described above in the general process for synthesis of Compound A, Compound B, Compound E and Compound F, the metal complex compound of the present invention represented by general formula (1) can be synthesized via a plurality of routes. The present invention will be described with reference to examples in the following. However, the compound and the device of the present invention are not limited to those described in the examples.

Example 1

Synthesis of Compound 1

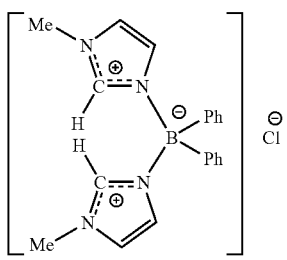

Compound 1

Under a stream of argon, 10 ml (0.01 mole) of a THF (tetrahydrofuran) solution of PhMgBr (phenylmagnesium bromide) adjusted at a concentration of 1.0 mole/liter was slowly added dropwise to a solution containing 1.59 g (0.01 moles) of phenyldichloroborane in 35 ml of THF under stirring at −78° C. When the addition was completed, the temperature was slowly raised to the room temperature over 1 hour, and the resultant solution was kept being stirred at the room temperature for 4 hours. To the resultant reaction solution, a THF solution (5 ml) of 1.64 g (0.02 moles) of 1-methylimidazole was slowly added dropwise under cooling with ice. When the addition was completed, the reaction solution was kept being stirred at the room temperature for 4 hours. The solvent (THF) was removed from the reaction solution under a reduced pressure, and Compound 1 (a crude product, containing magnesium salts) was obtained.

Example 2

Synthesis of Compound 2

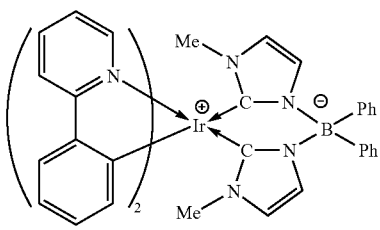

Compound 2

The reactions were conducted entirely under a stream of argon.

To Compound 1 obtained above in Example 1, 100 ml of 2-ethoxyethanol was added as the solvent, and a suspension was obtained <Fluid A>. Separately, to Compound 3 (5.36 g, 5×10⁻³ moles), 100 ml of 2-ethoxyethanol was added as the solvent, and then 3 equivalents (1.02 g, 1.5×10⁻² moles) of sodium ethoxide was added. The reaction was allowed to proceed in the resultant mixture at the room temperature for 5 hours <Fluid B>. The two fluids prepared above were mixed by adding <Fluid B> to <Fluid A>, and the reaction was allowed to proceed under the refluxing condition for 5 hours. 2-Ethoxyethanol of the solvent was removed from the obtained reaction mixture by distillation with heating under a vacuum. After the residue was cooled, about 30 ml of methylene chloride was added, and solid components were separated by filtration. Methylene chloride was removed by distillation under a vacuum, and Compound 2 was obtained as a crude product. The crude product was treated by fractionation by crystallization using methylene chloride and hexane, and 0.83 g (the yield: 10%) of Compound 2 was obtained. FD-MS of the obtained compound was measured, and the maximum peak was found at 828, which agreed with the calculated value. When the obtained compound was irradiated with an UV lamp (365 nm), emission of green light was observed.

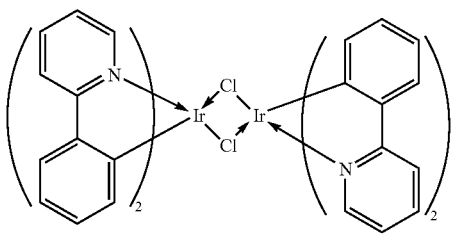

Compound 3

INDUSTRIAL APPLICABILITY

As described specifically in the above, the metal complex compound of the present invention can be used as the material for organic EL devices. The organic EL device using the compound exhibits a great efficiency of light emission and has a long life. The device can be advantageously applied to the fields such as various display devices, displays, back lights, light sources for illumination, marking signs, sign boards and interior products, and is particularly suitable as a display device for color display.

What is claimed is:

1. A metal complex compound having a metal-carbene bond represented by following general formula (1):

$$(L^1)_m M(L^2)_n \qquad (1)$$

[In general formula (1), M represents an iridium atom, $L^1$ and $L^2$ represent bidentate ligands different from each other, a partial structure represented by $(L^1)_m M$ is represented by following general formula (2), a partial structure represented by $M(L^2)_n$ is represented by following general formula (3), m represents an integer of 0 to 2, n represents an integer of 1 to 3, and m+n represents a valence of the metal represented by M

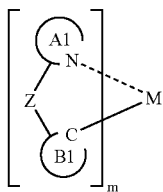

(2)

{In general formula (2), N and C represent nitrogen atom and carbon atom, respectively, ring A1 represents an aromatic heterocyclic group having 3 to 50 nuclear atoms including nitrogen atom which may have substituents, ring B1 represents an aryl group having 6 to 50 nuclear carbon atoms which may have substituents, and ring A1 and ring B1 are bonded with covalent bonds via Z, wherein Z represents a single bond, —O—, —S—, —CO—, —(CR'R'')$_a$—, —(SiR'R'')$_a$— or —NR'—, (R' and R'' each independently represent hydrogen atom, an aryl group having 6 to 50 nuclear carbon atoms which may have substituents, an aromatic heterocyclic group having 3 to 50 nuclear atoms which may have substituents or an alkyl group having 1 to 50 carbon atoms which may have substituents, a represents an integer of 1 to 10, and the atoms and the groups represented by R' and R'' may be a same with or different from each other)}

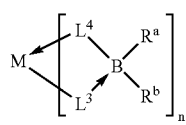

(3)

{In general formula (3), B represents boron atom, $L^3$ and $L^4$ each represent a crosslinking group having a covalent bond (shown by a solid line) and a coordinate bond (shown by an arrow), at least one of $L^3$ and $L^4$ represents an aromatic heterocyclic group having 3 to 50 nuclear atoms and nitrogen atom which has a coordinate bond with carbene carbon atom and may have substituents, $R^a$ and $R^b$ each independently represent hydrogen atom, an alkyl group having 1 to 50 carbon atoms which may have substituents, an alkenyl group having 2 to 50 carbon atoms which may have substituents, an aryl group having 6 to 50 nuclear carbon atoms which may have substituents or an aromatic heterocyclic group having 3 to 50 nuclear atoms which may have substituents, and groups represented by $L^3$, $L^4$, $R^a$ and $R^b$ may be bonded to each other to form a cyclic structure}].

2. A metal complex compound having a metal-carbene bond represented by following general formula (1):

$$(L^1)_m M(L^2)_n \qquad (1)$$

[In general formula (1), M represents an iridium atom or platinum atom, $L^1$ and $L^2$ represent bidentate ligands different from each other, a partial structure represented by $(L^1)_m M$ is represented by following general formula (4), a partial structure represented by $M(L^2)_n$ is represented by following general formula (3), m represents an integer of 0 to 2, n represents an integer of 1 to 3, and m+n represents a valence of the metal represented by M:

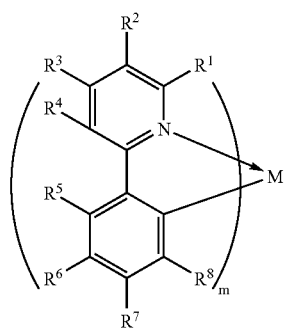

(4)

(In the above formula (4), $R^1$ to $R^8$ each independently represent hydrogen atom, an alkyl group having 1 to 30 carbon atoms which may have substituents, a halogenated alkyl group having 1 to 30 carbon atoms which may have substituents, an alkoxyl group having 1 to 30 carbon atoms which may have substituents, a heterocyclic group having 3 to 20 nuclear atoms which may have substituents, an aryl group having 6 to 40 nuclear carbon atoms which may have substituents, an aryloxyl group having 6 to 40 nuclear carbon atoms which may have substituents, an aralkyl group having 7 to 40 carbon atoms which may have substituents, an alkenyl group having 2 to 30 carbon atoms which may have substituents, an arylamino group 6 to 80 nuclear carbon atoms which may have substituents, an alkylamino group having 1 to 60 carbon atoms which may have substituents, an aralkylamino group having 7 to 80 carbon atoms which may have substituents, an alkylsilyl group having 1 to 30 carbon atoms which may have substituents, an arylsilyl group having 6 to 40 carbon atoms which may have substituents, a halogen atom, cyano group, nitro group, —S(R)O$_2$ or —S(R)O [R representing a substituent], and adjacent groups represented by $R^1$ to $R^8$ may be bonded to each other to form a cyclic structure),

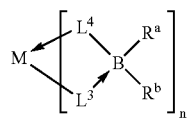

(3)

{In general formula (3), B represents boron atom, $L^3$ and $L^4$ each represent a crosslinking group having a covalent bond (shown by a solid line) and a coordinate bond (shown by an arrow), at least one of $L^3$ and $L^4$ represents an aromatic heterocyclic group having 3 to 50 nuclear atoms and nitrogen atom which has a coordinate bond with carbene carbon atom and may have substituents, $R^a$ and $R^b$ each independently represent hydrogen atom, an alkyl group having 1 to 50 carbon atoms which may have substituents, an alkenyl group having 2 to 50 carbon atoms which may have substituents, an aryl group having 6 to 50 nuclear carbon atoms which may have substituents or an aromatic heterocyclic group having 3 to 50 nuclear atoms which may have substituents, and groups represented by $L^3$, $L^4$, $R^a$ and $R^b$ may be bonded to each other to form a cyclic structure}].

3. A metal complex compound having a metal-carbene bond according to claim 1 or claim 2, wherein, in general formula (3) representing the partial structure represented by $M(L^2)_n$, at least one of $L^3$ and $L^4$ represents a partial structure represented by following general formula (5) or (6) or a limiting structure of resonance for the partial structure represented by general formula (5) or (6):

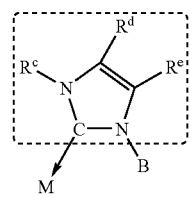

(5)

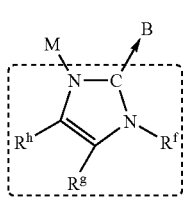

(6)

(an arrow in C (carbon atom)→M and C→B (boron atom) represents carbene bond, N represents nitrogen atom, $R^c$ to $R^h$ each independently represent hydrogen atom, an alkyl group having 1 to 50 carbon atoms which may have substituents, an alkenyl group having 2 to 50 carbon atoms which may have substituents, an aryl group having 6 to 50 nuclear carbon atoms which may have substituents or an aromatic heterocyclic group having 3 to 50 nuclear atoms which may have substituents, and adjacent groups may be bonded to each other to form a cyclic structure).

4. A metal complex compound having a metal-carbene bond according to claim 2, wherein M represents an iridium atom.

5. A metal complex compound having a metal-carbene bond according to claim 2, wherein M represents an iridium atom and, in general formula (3) representing the partial structure represented by $M(L^2)_n$, at least one of $L^3$ and $L^4$ represents a partial structure represented by following general formula (5) or (6) or a limiting structure of resonance for the partial structure represented by general formula (5) or (6):

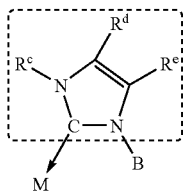

(5)

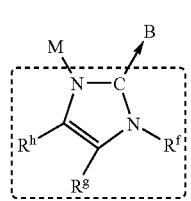

(6)

(an arrow in C (carbon atom)→M and C→B (boron atom) represents carbene bond, N represents nitrogen atom, $R^c$ to $R^h$ each independently represent hydrogen atom, an alkyl group having 1 to 50 carbon atoms which may have substituents, an alkenyl group having 2 to 50 carbon atoms which may have substituents, an aryl group having 6 to 50 nuclear carbon atoms which may have substituents or an aromatic heterocyclic group having 3 to 50 nuclear atoms which may have substituents, and adjacent groups may be bonded to each other to form a cyclic structure).

6. A metal complex compound having a metal-carbene bond according to claim 1, wherein m is 1 or 2 in general formula (2).

7. A metal complex compound having a metal-carbene bond according to claim 1, wherein m is 2 in general formula (2) and n is 1 in general formula (3).

8. A metal complex compound having a metal-carbene bond according to claim 2, wherein M represents a platinum atom.

* * * * *